United States Patent
Bar-Tal et al.

(10) Patent No.: US 10,314,542 B2
(45) Date of Patent: Jun. 11, 2019

(54) IDENTIFICATION OF FRACTIONATED SIGNALS

(71) Applicant: Biosense Webster (Israel) Ltd., Yokneam (IL)

(72) Inventors: Meir Bar-Tal, Haifa (IL); Richard P. M. Houben, Lanaken (BE); Yaniv Ben Zrihem, Binyamina (IL); Stanislav Goldberg, Haifa (IL); Roy Urman, Karkur (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 155 days.

(21) Appl. No.: 15/404,244

(22) Filed: Jan. 12, 2017

(65) Prior Publication Data

US 2017/0202516 A1    Jul. 20, 2017

Related U.S. Application Data

(60) Provisional application No. 62/278,676, filed on Jan. 14, 2016.

(51) Int. Cl.
*A61B 5/00*   (2006.01)
*A61B 5/044*   (2006.01)
(Continued)

(52) U.S. Cl.
CPC .......... *A61B 5/6852* (2013.01); *A61B 5/0402* (2013.01); *A61B 5/044* (2013.01);
(Continued)

(58) Field of Classification Search
CPC ..... A61B 5/6852; A61B 5/046; A61B 5/0422; A61B 5/04012; A61B 5/0402; A61B 5/04525; A61B 5/0452; A61B 5/044
See application file for complete search history.

(56) References Cited

U.S. PATENT DOCUMENTS 6,973,339 B2   12/2005   Govari
8,433,398 B2   4/2013   Zhang
(Continued)

FOREIGN PATENT DOCUMENTS

CN   101156774 A   4/2008
EP   2 984 986 A2   2/2016

OTHER PUBLICATIONS

Narayan, et al. "Classifying Fractionated Electrograms in Human Atrial Fibrillation Using Monophasic Action Potentials and Activation Mapping: Evidence for Localized Drivers, Rate Acceleration, and Nonlocal Signal Etiologies," Heart Rhythm, Elsevier, US, vol. 8, No. 2, Oct. 11, 2010, pp. 244-253.
(Continued)

*Primary Examiner* — Mark Bockelman
(74) *Attorney, Agent, or Firm* — Volpe and Koenig, P.C.

(57) ABSTRACT

A system and method of determining regions of interest for heart ablation using fractionation. The method can comprise detecting, via sensors, electro-cardiogram (ECG) signals, each ECG signal detected via one of the sensors and indicating electrical activity of a heart, determining, for each of the ECG signals, activation times (LATs) each indicating a time of activation of a corresponding ECG signal, generating, based on the determined LATs of each of the ECG signals, one or more driver maps and one or more perpetuator maps, each representing the electrical activity of the heart, deriving parameters from the driver and perpetuator maps, using at least fractionation, processing and combining the derived parameters into driver evidence and perpetuator evidence, and determining the regions of interest for heart ablation in accordance with the fractionation used to derive the driver evidence and the perpetuator evidence.

14 Claims, 30 Drawing Sheets

(51) Int. Cl.
  *A61B 5/0402*   (2006.01)
  *A61B 5/0452*   (2006.01)
  *A61B 5/04*     (2006.01)
  *A61B 5/042*    (2006.01)
  *A61B 5/046*    (2006.01)

(52) U.S. Cl.
  CPC .......... *A61B 5/046* (2013.01); *A61B 5/04012* (2013.01); *A61B 5/0422* (2013.01); *A61B 5/0452* (2013.01); *A61B 5/04525* (2013.01)

(56) References Cited

U.S. PATENT DOCUMENTS

| | | |
|---|---|---|
| 2002/0022839 A1 | 2/2002 | Stewart et al. |
| 2002/0055674 A1 | 5/2002 | Ben-Haim et al. |
| 2004/0059237 A1 | 3/2004 | Narayan et al. |
| 2004/0243012 A1 | 12/2004 | Ciaccio et al. |
| 2005/0038333 A1 | 2/2005 | Sra |
| 2007/0197929 A1 | 8/2007 | Porath et al. |
| 2008/0188765 A1 | 8/2008 | Stolarski et al. |
| 2009/0112199 A1 | 4/2009 | Zhang et al. |
| 2009/0253974 A1 | 10/2009 | Rahme |
| 2011/0054560 A1 | 3/2011 | Rosenberg et al. |
| 2011/0125041 A1 | 5/2011 | Fischell et al. |
| 2011/0230775 A1 | 9/2011 | Barley et al. |
| 2011/0251505 A1 | 10/2011 | Narayan et al. |
| 2013/0006131 A1 | 1/2013 | Narayan et al. |
| 2013/0131746 A1 | 5/2013 | Simon et al. |
| 2013/0274582 A1 | 10/2013 | Afonso et al. |
| 2014/0005563 A1 | 1/2014 | Ramanathan et al. |
| 2014/0052118 A1 | 2/2014 | Laske et al. |
| 2014/0336520 A1 | 11/2014 | Zeng et al. |
| 2015/0216435 A1 | 8/2015 | Bokan et al. |
| 2015/0216438 A1 | 8/2015 | Bokan et al. |
| 2016/0045123 A1 | 2/2016 | Bar-Tal et al. |

OTHER PUBLICATIONS

European Search Report for EP17151686.7-1657, dated Jun. 2, 2017.
European Search Report for EP17151635.4-1657, dated May 31, 2017.
European Search Report for EP17151641.2-1657, dated May 26, 2017.
European Search Report for EP17151634.7-1657, dated May 29, 2017.
Allessie et al., "Electropathological substrate of long-standing persistent atrial fibrillation in patients with structural heart disease: Longitudinal Dissociation," Circulation—Arrhythmia and Electrophysiology, pp. 606-615 (Dec. 2010).
De Groot et al., "Electropathological Substrate of Longstanding Persistent Atrial Fibrillation in Patients With Structural Heart Disease: Epicardial Breakthrough," Circulation, pp. 1674-1682 (Oct. 26, 2010).
Houben et al., "S-wave predominance of epicardial electrograms during atrial fibrillation in humans: Indirect evidence for a role of the thin subepicardial layer," Heart Rhythm, vol. 1, No. 6, pp. 639-647 (Dec. 2004).
Inoue et al., "Trigger-based mechanism of the persistence of atrial fibrillation and its impact on the efficacy of catheter ablation," Circulation—Arrhythmia and Electrophysiology, pp. 295-301 (Apr. 2012).
Lee et al., "Simultaneous Bi-Atrial High Density (510-512 Electrodes) Epicardial Mapping of Persistent and Long-Standing Persistent Atrial Fibrillation in Patients: New Insights into the Mechanism of Its Maintenance," Circulation, vol. 132, Issue 22, pp. 2108-2117 (Dec. 1, 2015).

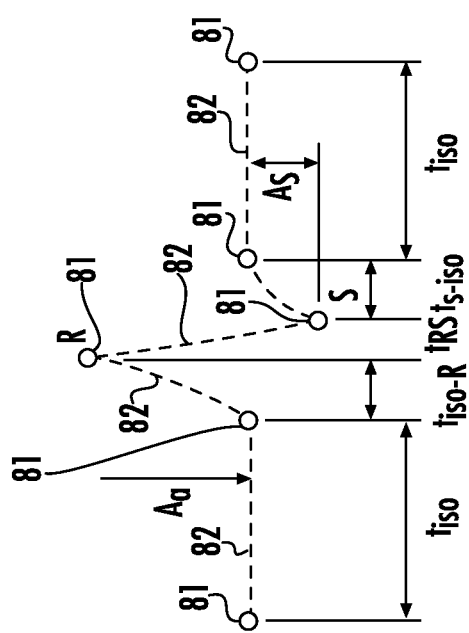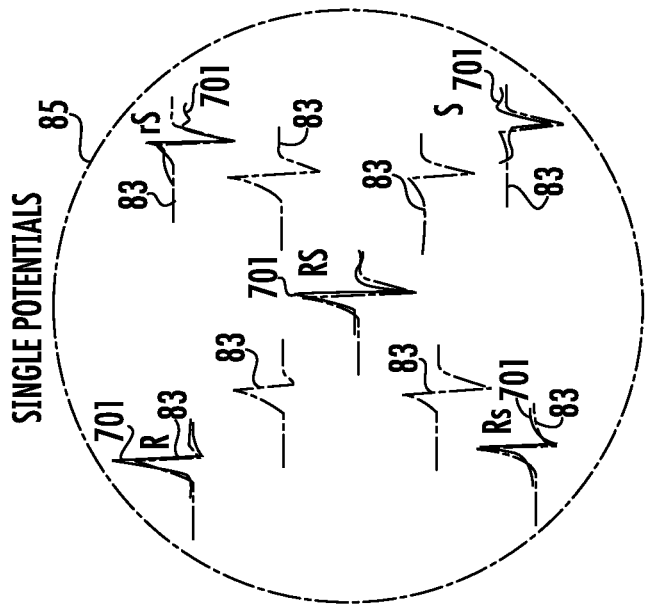
FIG. 8

TIME GATE: TEMPORAL GROUPING OF PRIMARY AND SECONDARY SLOPES

- NON CONTACT
  - ANALYZE 3X3 SPATIOTEMPORAL TIME WINDOW
  - FFLD SLOPE ANNOTATION
    - → FAR FIELD POTENTIAL
    - → NON-CONTACT
  - ANALYZE SLOPE ANNOTATION WITHIN WINDOW (t+/-W)
    - NO PRIMARY SLOPES FOUND IN CENTER ELECTRODE IC ECG
      - NON CONTACT EVIDENCE ++
    - + ONLY FAR FIELD SLOPES FOUND IN NEIGHBORING ELECTRODES→NON CONTACT EVIDENCE ++
    - + PRIMARY SLOPES FOUND IN NEIGHBORING ELECTRODES→NON CONTACT EVIDENCE ++
    - PRIMARY SLOPES FOUND IN CENTER ELECTRODE IC ECG
      - FF POTENTIAL EVIDENCE ++
    - + SYNCHRONOUS PRIMARY SLOPES FOUND IN NEIGHBORING ELECTRODES→NON CONTACT EVIDENCE ++

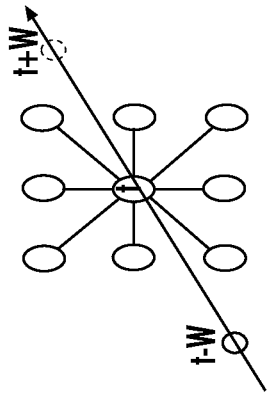

FIG. 23

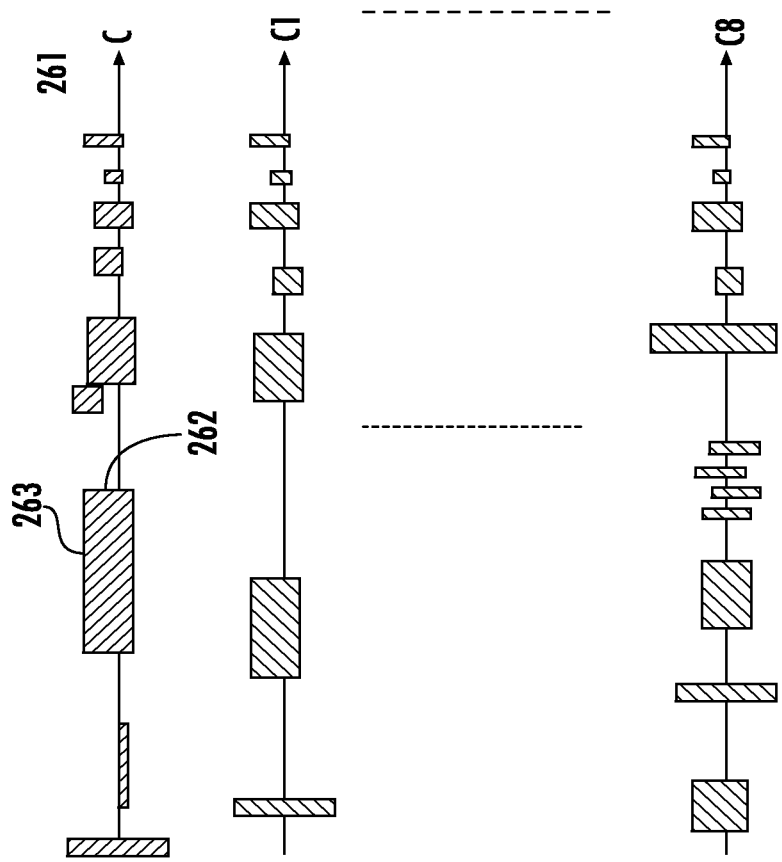
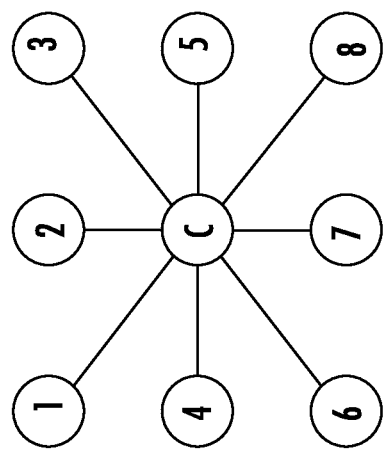
FIG. 26

IDENTIFICATION OF FRACTIONATED SIGNALS

CROSS REFERENCE TO RELATED APPLICATIONS

This application claims the benefit of U.S. Provisional Application No. 62/278,676, filed Jan. 14, 2016, which is incorporated by reference as if fully set forth. This application incorporates by reference as if fully set forth U.S. patent application Ser. No. 15/404,228 titled "Region of Interest Focal Source Detection Using Comparisons of R-S Wave Magnitudes and LATs of RS Complexes," U.S. patent application Ser. No. 15/404,225 titled "Region of Interest Rotational Activity Pattern Detection," U.S. patent application Ser. No. 15/404,226 titled "Overall System and Method for Detecting Regions of Interest," U.S. patent application Ser. No. 15/404,231 titled "Non-Overlapping Loop-Type or Spline-Type Catheter To Determine Activation Source Direction and Activation Source Type," and U.S. patent application Ser. No. 15/404,266 titled "Region of Interest Focal Source Detection," all filed on Jan. 12, 2017.

FIELD OF THE INVENTION

The present invention relates to systems and methods for determining regions of interest to be ablated for treatment of cardiac arrhythmia, such as atrial fibrillation. More particularly, the invention relates to improvements in analysis of intracardiac electrocardiography (ECG) signals to improve activation maps and better determine regions of interest.

BACKGROUND

Cardiac arrhythmia includes different types of abnormal or irregular heart rhythms, such as, for example, atrial fibrillation (AF), which is characterized by rapid and irregular beating. Under normal heart conditions, a heartbeat is produced by electrical pulses (i.e., signals) which originate in the upper chambers (i.e., atria) of the heart and pass through the atria through the atrioventricular (AV) node to a pair of lower chambers (i.e., ventricles) of the heart. As the signals pass through the atria, the atria contract and pump blood through the AV node into the ventricles. This causes the ventricles to contract, pumping out blood from the heart to the body. During conditions of AF, however, the signals in the atria become chaotic and cause the heart to beat irregularly.

AF can negatively affect the physical, psychological and emotional quality of a person's life. AF can progressively increase in severity and frequency and, if left untreated, may lead to chronic fatigue, congestive heart failure or stroke. One type of AF treatment includes prescribed medications, such as rhythm control medications and medications used to manage the increased risk of stroke. These medications must be taken daily and indefinitely. Another type of AF treatment includes cardioversion, which attempts to restore a normal heart rhythm by providing electric shocks to the heart through electrodes placed on the chest. In some persistent types of AF, cardioversion is either ineffective or cannot be attempted.

Recent approaches for treating AF include minimally invasive ablation procedures (e.g., catheter ablation) in which the heart tissue is ablated to terminate electrical pathways and block faulty electrical impulses that can cause heart rhythm disorders.

SUMMARY

A method may be used to determine one or more regions of interest for cardiac ablation using fractionation. For example, the method may detect, using one or more sensors, electro-cardiogram (ECG) signals. Each detected ECG signal may indicate electrical activity of a heart. The method may next determine, for each of the plurality of ECG signals, one or more local activation times (LATs). Each LAT may indicate a time of activation of a corresponding ECG signal.

The method may then generate, based on the determined one or more LATs, one or more driver maps. In addition, the method may also generate one or more perpetuator maps, each representing the electrical activity of the heart. The driver map and/or perpetuator map may be used to derive parameter using at least fractionation. The the derived parameters may then be processed and combined into driver evidence and perpetuator evidence. Finally, the method may determine the regions of interest for cardiac ablation in accordance with the fractionation used to derive the driver evidence and the perpetuator evidence.

A system may be used to determine one or more regions of interest for cardiac ablation using fractionation. The system may include a plurality of sensors, each sensor configured to detect a plurality of electro-cardiogram (ECG) signals over time. Each ECG signal may indicate electrical activity of a heart.

The system may include a processing device comprising one or more processors. Each processor may be configured to determine, for each of the plurality of ECG signals, one or more local activation times (LATs). Each LAT may indicate a time of activation of a corresponding ECG signal. Each processor may generate, based on the determined one or more LATs of each of the plurality of ECG signals, one or more driver maps. Each processor may further generate one or more perpetuator maps, each representing the electrical activity of the heart.

Each processor may derive parameters from the driver and perpetuator maps, using at least fractionation. Each processor may then process and combine the derived parameters into driver evidence and perpetuator evidence. Each processor may then determine the regions of interest for cardiac ablation in accordance with the fractionation used to derive the driver evidence and the perpetuator evidence and display the regions of interest information on a display device.

A computer software product may include a non-transitory computer readable storage medium in which computer program instructions are stored. The instructions, when executed by a computer, may cause the computer to perform one or more steps.

For example, the computer may perform a detection step, via a plurality of sensors, electro-cardiogram (ECG) signals, each ECG signal detected via one of the plurality of sensors and indicating electrical activity of a heart. The computer may also perform a determining step, for each of the plurality of ECG signals, one or more local activation times (LATs) each indicating a time of activation of a corresponding ECG signal.

The computer software product may cause the computer to generate, based on the determined one or more LATs of each of the plurality of ECG signals, one or more driver maps. The computer software product may cause the computer to also generate one or more perpetuator maps, each representing the electrical activity of the heart.

The computer software product may cause the computer to derive parameters from the driver and perpetuator maps, using at least fractionation. The computer software product may cause the computer to process and combine the derived parameters into driver evidence and perpetuator evidence. Finally, the computer software product may cause the computer to determine the regions of interest for cardiac ablation in accordance with the fractionation used to derive the driver evidence and the perpetuator evidence.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals.

FIGS. 7-11 illustrate AF Mapping to Appoint Ablation ROIs.

FIG. 23 further illustrates time gate and temporal grouping of primary and secondary slopes.

FIG. 26 illustrates the spatio-temporal analysis of identified slopes represented as rectangles.

DETAILED DESCRIPTION OF THE INVENTION

Conventional methods and systems used for catheter ablation typically include inserting the catheter through an incision in the skin and guided up to the heart. Before ablation is performed, intra-cardiac electrocardiogram (IC ECG) signals of the heart are acquired via electrodes placed at different areas of the heart. The signals are monitored and used to provide information to determine whether one or more areas of the heart are causing the irregular heart rhythm. The conventional methods and systems used to determine these areas to be ablated, however, are time consuming (e.g., several hours) and rely on medical personnel with specific expertise and experience (typically requiring many hours of training).

Embodiments disclosed herein employ systems, apparatuses and methods of determining potential regions of interest (ROIs) to be targeted for ablation. Various mapping techniques are utilized to provide maps of the electrophysical conditions of the AF substrate and maps representing a spatio-temporal manifestation of the AF process to provide efficient and accurate determination of potential ablation ROIs. Mapping techniques utilize various parameters (e.g., cycle, earliness, R-S complex, conduction velocity (CV), block and fractionation) of acquired IC ECG signals and detected local activation times (LATs) to identify potential evidence of drivers and perpetuators of the AF substrate. Identification of the potential evidence of drivers and perpetuators is used to provide mapping (e.g., driver maps and perpetuator maps) of the AF substrate. Mapping techniques also include utilizing the various parameters of the acquired IC ECG signals and detected local activation times to provide mapping (e.g., activation/wave maps, CV maps, fractionation maps, voltage maps and block maps) which potentially represents the spatio-temporal manifestation of the AF process. The mapping of the spatio-temporal manifestation of the AF process can be used in addition to, or alternative to, the mapping of the AF substrate to identify potential ablation ROIs. The mapping techniques are used to potentially reduce AF map analysis training time, increase success rates resulting from ablation and facilitate efficient interpretation of AF maps. For simplification purposes, embodiments described herein refer to systems and methods used for the treatment of AF. It is noted however, embodiments may be used for the treatment of any type of cardiac arrhythmia including different types of abnormal or irregular heart rhythms.

Figure 1:
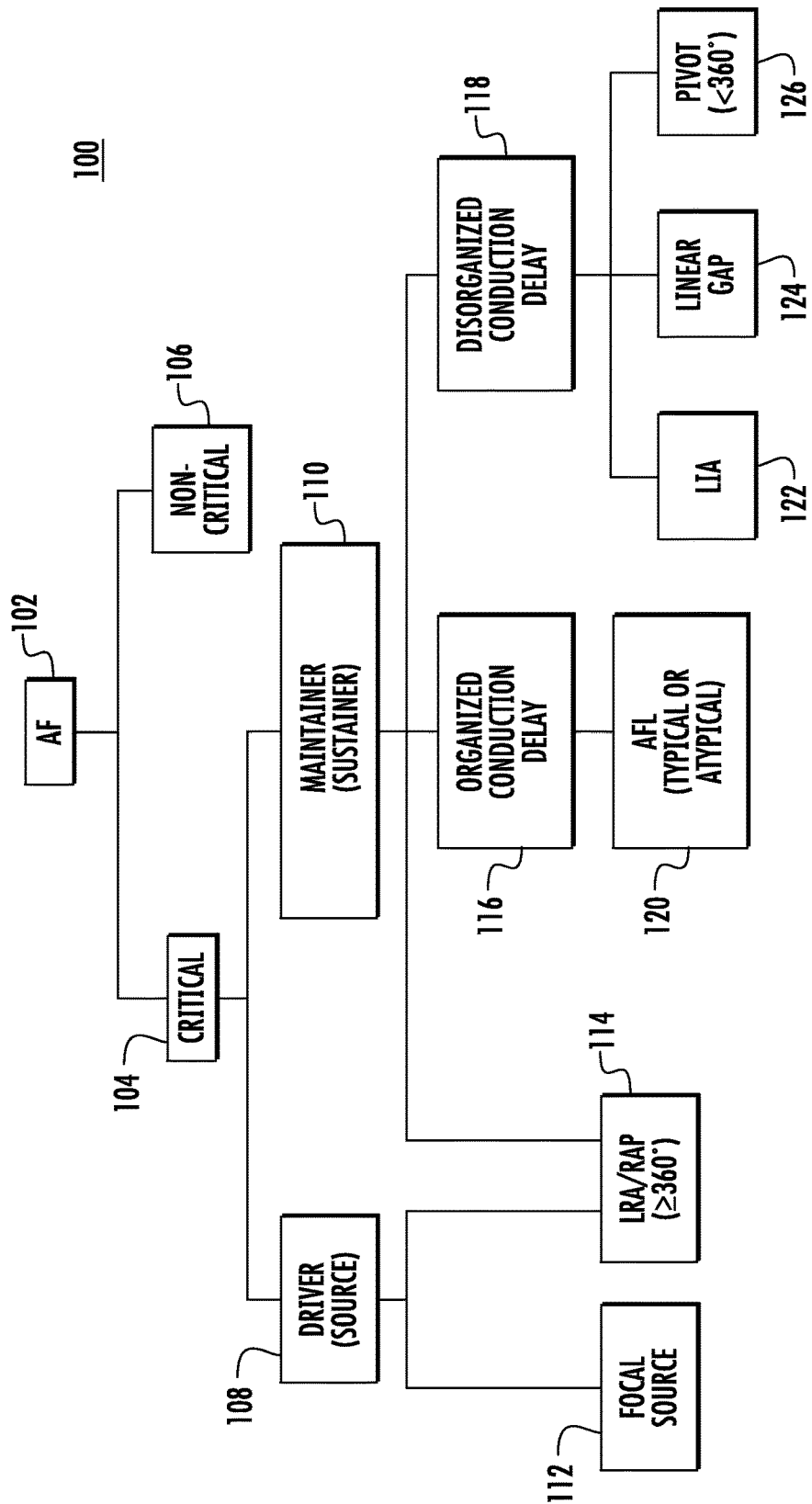
FIG. 1 is a block diagram illustrating an exemplary classification of AF used with embodiments disclosed herein.

FIG. 1 is a block diagram illustrating an exemplary classification of AF used with embodiments disclosed herein. The exemplary classification in FIG. 1 distinguishes between critical and non-critical AF as well as between drivers and perpetuators of AF and their relative spatiotemporal patterns.

For example, as shown in FIG. 1, an irregular heart rhythm characterized as AF 102 is classified as critical 104 or non-critical 106. Examples of non-critical AF 106 include paroxysmal (i.e., intermittent) irregular heart rhythm episodes in which the heartbeat often normalizes as quickly as within a few seconds or after a few hours, and persistent irregular heart rhythm episodes in which a normal heart may be restored by rhythm medical therapy or a procedure (e.g., cardioversion). Examples of critical AF 104 include longstanding persistent irregular heart rhythm episodes that continue for longer periods of time (e.g., more than a year) in which the heart is in a constant state of AF and the condition is considered permanent.

Critical AF can be classified according to characteristics (e.g., areas of activation) that can be derived from IC ECG signals. Areas of activation may be identified as potential contributing factors to AF. As shown in FIG. 1, critical AF is classified according to different areas of activation, including a potential driver of AF (hereinafter "driver") or potential source of AF (hereinafter "source") 108 and a potential perpetuator 110 of AF (hereinafter "perpetuator"). A driver 108 is an area of activation (e.g., in the atria) where electrical pulses originate to stimulate the heart to contract and which can potentially contribute to AF, for example, by producing fibrillatory conduction to other areas of the atria. A perpetuator 110 is an area of sustained activation (e.g., electrophysiological process/substrate) which can also potentially contribute to AF.

Drivers 108 and perpetuators 110 may be represented (e.g., mapped) according to their spatio-temporal manifestation. As shown in FIG. 1, drivers 108 and perpetuators 110 are classified by exemplary spatio-temporal manifestation types, including focal sources (foci) 112 and localized rotational activation (LRA) sources or rotational activation patterns (RAPs) sources 114. A focal source is a type of driver originating at a small area of the atria which spreads centrifugally from a single point. A RAP 114 source is an irregular region of the heart where the electrical pulses rotate at least 360 degrees about a center area.

FIG. 1 also shows different types of perpetuators 110, including one type which exhibits organized conduction delay 116 and another which exhibits disorganized conduction delay 118. Another type of perpetuator 110 shown in FIG. 1 includes atrial flutter (AFL) 120 characterized by organized conduction delay 116 as well as localized irregular activation (LIA) 122, linear gaps 124 and pivots 126 (i.e., electrical pulses that rotate less than 360 degrees about a center area) characterized by disorganized conduction delay 118. Also, the RAP source 114 is shown as both a driver 108 and a perpetuator 110. Drivers 108 and perpetuators 110 are, for example, separately mapped to facilitate identification of driver types and/or perpetuator types and provide efficient and accurate determination of potential ablation ROIs.

Mapping and identification of drivers 108 and perpetuators 110 can also be based on one or more additional factors which may potentially contribute to AF or parameters which may potentially characterize the AF substrate (i.e., the AF process itself) and/or the manifestation of the AF process. For example, AF parameters or AF factors used to identify potential focal sources 108 include omnidirectional activation spread of activation from a point, earliness (e.g., focal source which starts after an excitable gap), triggers such as fast firing (e.g., short cycle-length and high dominant frequency) foci and breakthroughs (e.g., pulmonary veins (PV), free wall and transmural, endocardial and epicardial) and micro re-entry circuit which manifests as focal source and short-radius re-entry circuits which can manifest as a driver 108 depending on the specific anisotropic structure of the central obstacle.

AF parameters or AF factors used to map and identify RAP sources 114 include, for example, repetitive cycles, rotors which can manifest as a driver source 108, structural or functional anisotropy (e.g., localized or distributed), and short-radius re-entry circuits which can manifest as either a driver 108 or a perpetuator 110, depending on specific anisotropic structure of the central obstacle.

AF parameters or AF factors used to map and identify perpetuators 110 include, for example, extension (increased) path length, anatomical (pathological) block lines, fibrosis, stable functional block lines (e.g., areas of prolonged refractoriness), criticality (e.g., shortest path around block line>path length) and fibrillatory conduction factors (e.g., dissociated waves, re-entry circuit factors).

Figure 2:
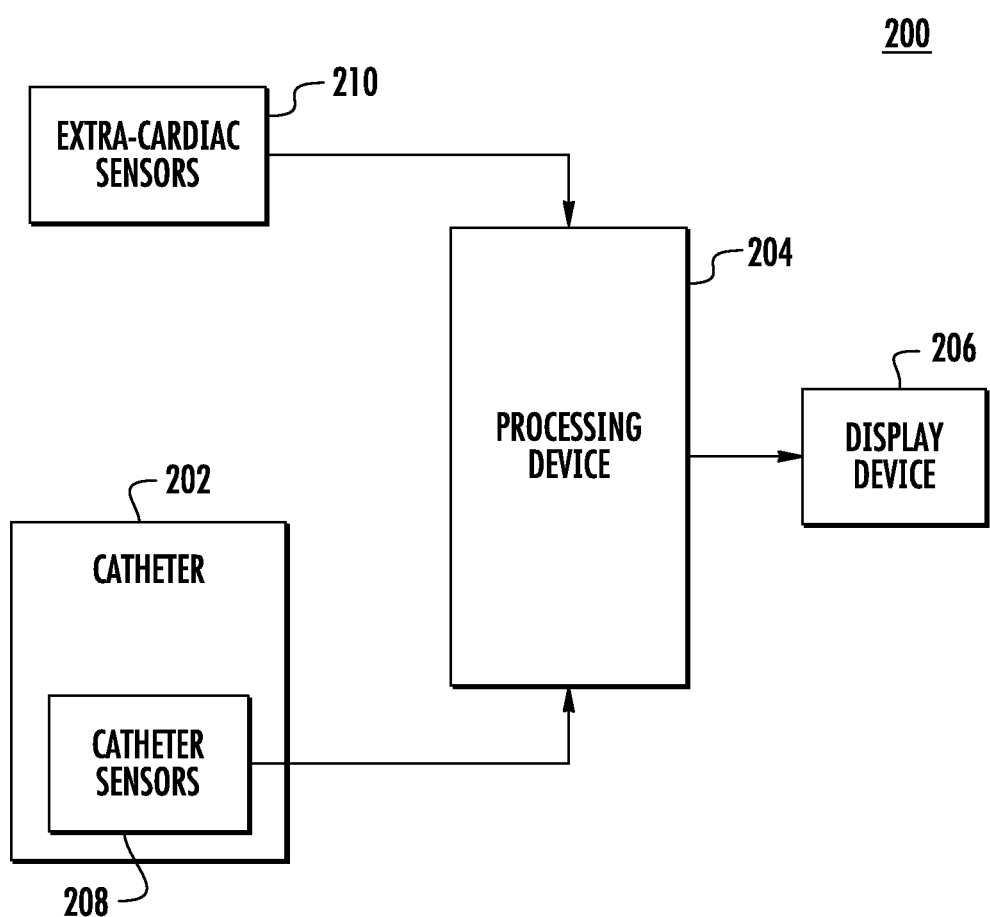
FIG. 2 is a block diagram illustrating an exemplary system used to determine AF ROIs for ablation for use with embodiments disclosed herein.

FIG. 2 is a block diagram illustrating an exemplary system 200 used to determine AF ROIs for ablation for use with embodiments disclosed herein. As shown in FIG. 2, the system 200 includes a catheter 202, a processing device 204 and a display device 206. Catheter 202 includes an array of catheter sensors (e.g., electrodes) each configured to detect electrical activity (electrical signals) of an area of the heart over time. When an IC ECG is performed, each electrode detects the electrical activity of an area of the heart in contact with the electrode. The system 200 also includes extra-cardiac sensors 210 (e.g., electrodes on the skin of a patient) configured to detect electrical activity of the heart via detection of electrical changes on the skin due to the electro-physiologic pattern of the heart.

The detected IC ECG signals and the detected extra-cardiac signals are processed (e.g., recorded over time, filtered, fractionated, mapped, combined, interpolated, etc.) by processing device 204 and displayed on display device 206.

Embodiments may include any number of sensors 210 used to detect ECG signals, including sensors used to detect IC ECG signals and extra-cardiac ECG signals. For simplification purposes, systems and methods described herein refer to the detection and use of IC ECG signals. It is noted, however, that embodiments may utilize IC ECG signals or extra-cardiac ECG signals or a combination of both IC ECG signals and extra-cardiac ECG signals.

Processing device 204 may include one or more processors each configured to process the ECG signals. Each processor of processing device 204 may be configured to record ECG signals over time, filter ECG signals, fractionate ECG signals into signal components (e.g., slopes, waves, complexes), map ECG signals, combine ECG signal information, map and interpolate mapping information, etc.

Display device 206 may include one or more displays each configured to display ECG signals, ECG signal information, maps of the AF process and maps representing a spatio-temporal manifestation of the AF process.

The catheter sensors 208 and the extra cardiac sensors 210 may be in wired or wireless communication with processing device 204. Display device 206 may also be in wired or wireless communication with processing device 204.

Figure 3A:
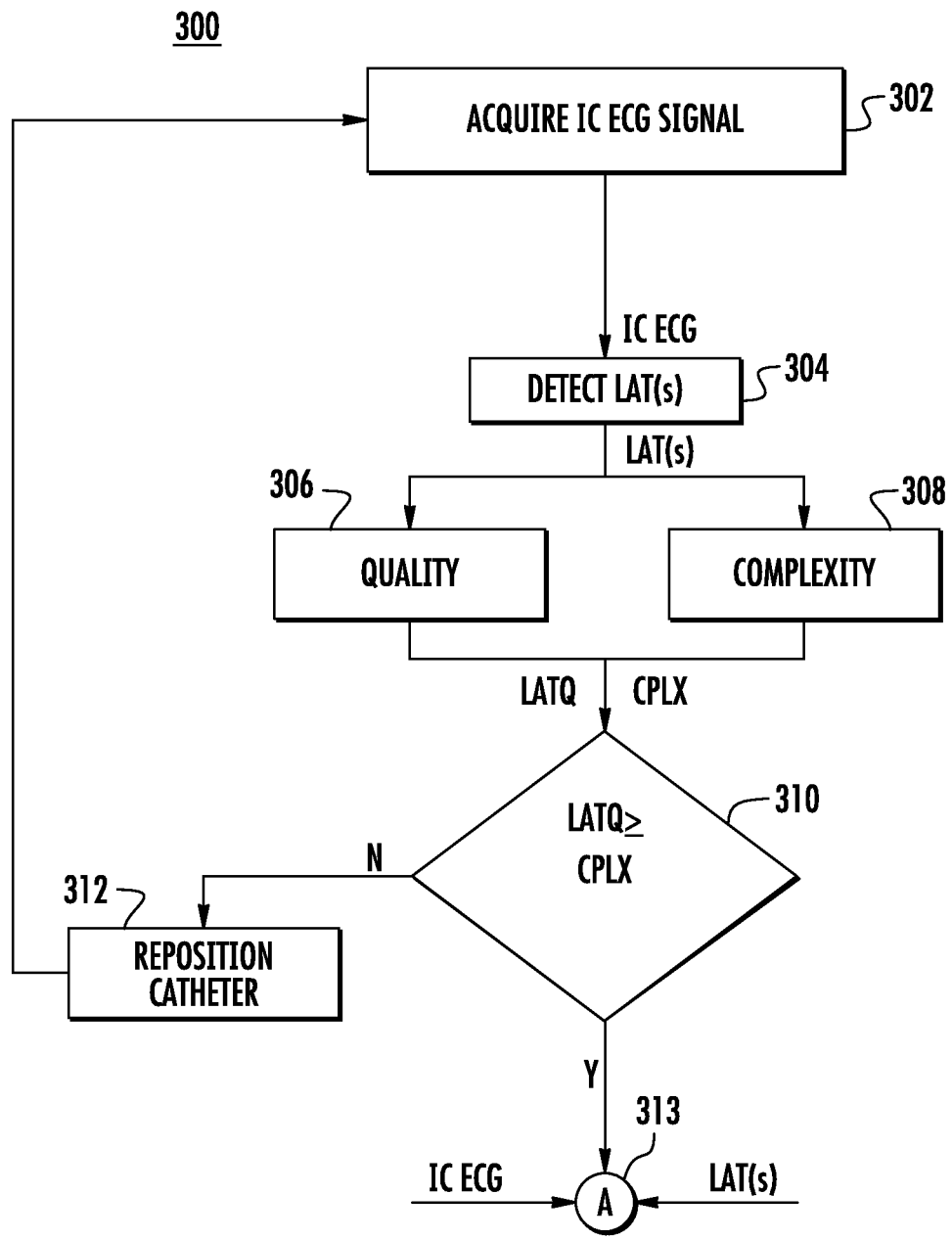
FIGS. 3A and 3B are portions of a flow diagram illustrating an exemplary method of determining an AF ROI for ablation according to an embodiment.
Figure 3B:
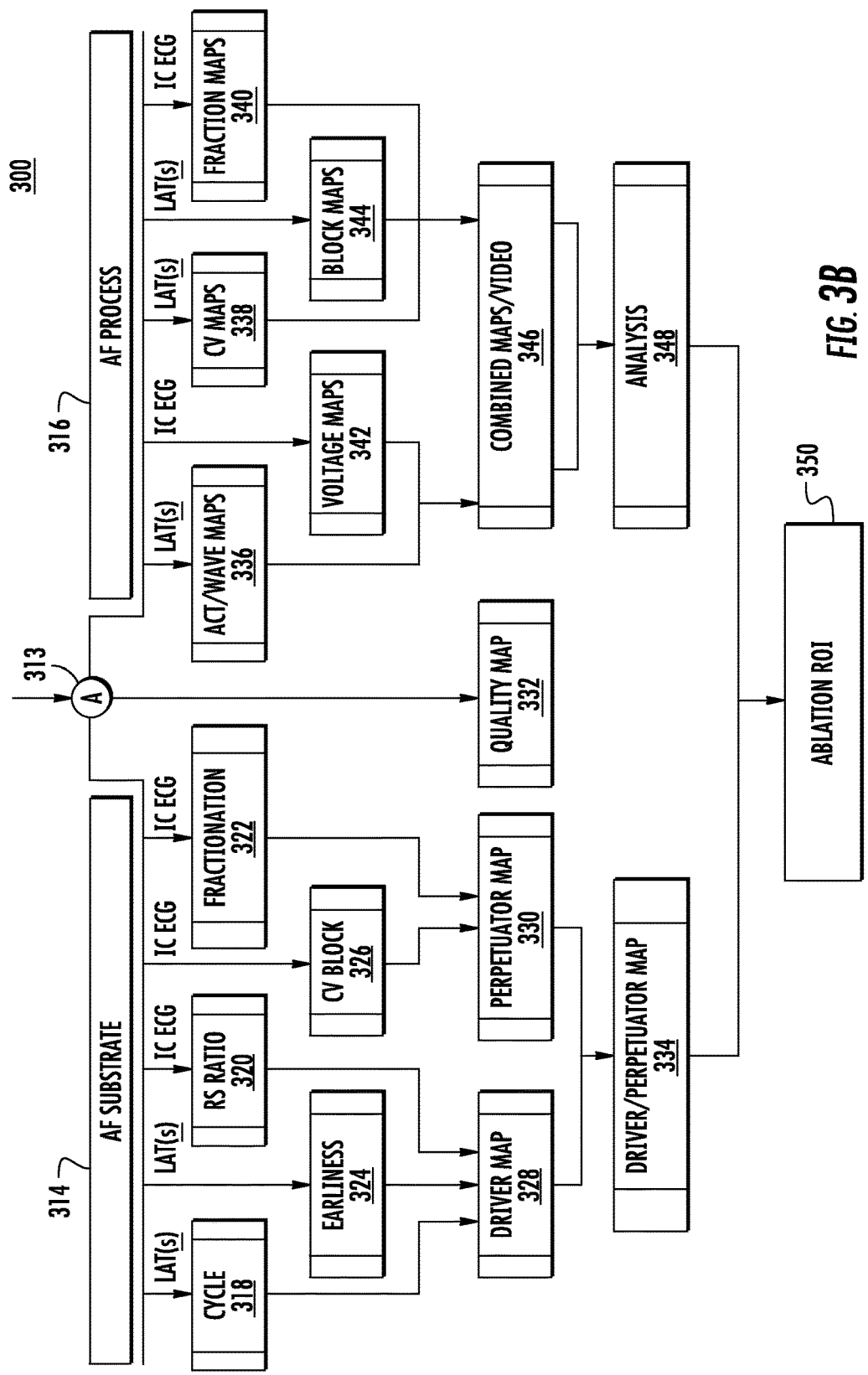

FIGS. 3A and 3B are portions of a flow diagram illustrating an exemplary method 300 of determining a potential ablation ROI. The method 300 employs a mapping taxonomy which includes, from its core moving outward, an IC ECG layer, a pre-processing layer, a LAT detection layer, a map segmentation layer, a map interpolation layer and a map interpretation layer.

FIG. 3A illustrates a portion of exemplary method 300. As shown in block 302 of FIG. 3A, the method 300 includes, as part of the IC ECG layer, acquiring an IC ECG signal which represents electrical activity of an area of the heart. The IC ECG signal acquired at block 302 is, for example, acquired from one of a number of electrodes in contact with different areas of the heart. After acquisition of the IC ECG (302), the method 300 includes, as part of the pre-processing layer, pre-processing of the acquired ECG signal, as shown in block 302 of FIG. 3A, The pre-processing may include execution of one or more algorithms, such as for example, cancellation of ventricular far field signals, baseline correction, and noise reduction. Ventricular far field detection may include, for example, a spatial averaging method (SAM), a temporal averaging method (TAM), a system identification method (SIM) and principal component analysis (PCA).

For each IC ECG signal acquired at block 302, one or more LATs of the corresponding pre-processed IC ECG signal is (are) detected at block 304. The LAT quality (shown as LATQ in FIG. 3A) of each signal is determined at block 306 as part of an exemplary LAT detection layer. The AF complexity (shown as CPLX in FIG. 3A) of the signal is determined at block 308.

As shown at decision point 310, the method 300 includes determining whether to reposition the catheter based on the LAT quality of the signal and the AF complexity. A typical characteristic of high quality IC ECGs is little base line wander (e.g., low baseline vs. IC ECG RMS amplitude, limited ventricular far-field potentials vs. IC ECG RMS amplitude). IC ECG signals characteristics include discernable atrial complexes (e.g., confined (~50 ms) complexes separated by isoelectric segments repeating slopes, 50-200 ms interval; about 150 ms median) during AF. High quality complexes characteristic typically have considerable amplitudes and steep downward slopes (vs. upward slopes) within complexes. Characteristics of the IC ECG signals may be combined into a single measurable characteristic or parameter (e.g., having a measurable value of 0%-100%) to define LAT quality. The LAT quality may be compared to the AF complexity to determine whether to reposition the catheter.

In some embodiments, quality is defined by an ability to map AF for a level of AF complexity. Determining whether to reposition the catheter may include generating a map and determining whether the generated map can be used (e.g., is adequate) to map AF based on whether a level of coverage of a mapping electrode meets (e.g., matches) a level of AF complexity. The ability to map AF for a level of AF complexity may include meeting a map threshold level (e.g., adequate level, trustworthy level). A single parameter (i.e., mapping coverage) is used to define a level of coverage of the mapping electrode. Examples of characteristics that are combined to define the mapping coverage include: (1) contact of the mapping electrode (e.g., contact with active tissue (wall) related to covered area and LAT accuracy); (2) resolution of the electrodes (e.g., distances and electrode sensitivity radii between electrodes, including mean, minimum and maximum and distances); and (3) quality of the IC ECG and associated annotations provided by a detection algorithm.

AF complexity may include complexity of activation during AF creating wave dissociation (block lines), fusion and wave curvature. Accordingly, a map may be determined as a map which can be used (e.g., trustworthy or adequate) to map AF when, given a certain level of AF complexity (e.g., measured along y-axis), the mapping coverage (including signal and annotation quality measured along x-axis) is sufficient to map the AF complexity. If not, the trustworthiness of the map may become compromised or inadequate.

Signals may then be analyzed using the trustworthy or adequate maps to determine whether the catheter should be repositioned. If it is determined at decision point 310 to reposition the catheter, the catheter (e.g., catheter 202) is repositioned at block 312 and a new IC ECG signal is acquired at block 302. If it is determined at decision point 310 that the catheter should be repositioned, the method 300 continues to "point A" 313 (shown in FIG. 3A and FIG. 3B).

FIG. 3A illustrates the acquiring of a single IC ECG signal for simplification purposes. In practice, however, multiple signals are acquired for each of the plurality of electrodes contacting the heart. Each IC ECG signal acquired at block 202 and the one or more LATs detected for each signal at block 204 are received at "point A" 313.

FIG. 3B illustrates exemplary methods which may be used to determine potential ablation ROIs. As shown FIG. 3B, each acquired IC ECG signal and the one or more detected LATs for each signal are used to generate maps of the AF process that includes the electro-physical conditions of the AF substrate (indicated as the AF Substrate 314 in FIG. 3B) and maps representing a spatio-temporal manifestation of the AF process (indicated as the AF Process 316 in FIG. 3B) as part of an exemplary map segmentation layer.

For example, with regard to the AF Substrate 314 shown in FIG. 3B, the one or more detected LATs are used to independently determine one or more factors or parameters which may contribute to AF. The left side of FIG. 3B illustrates methods which characterize the AF substrate by collecting information over a predefined window of time while assessing a mean interval (e.g., cycle) based on a difference of subsequent LATs 318, first activated (earliness) 324, and morphological aspects of the IC ECG including RS-ratio 320 and fractionation 322 (e.g., fractionated electrograms). For example, the detected LATs are used to independently determine cycle information (e.g., cycle lengths) at block 318 and earliness information (e.g., earliest activation times, early drivers which start after an excitable gap) at block 324. Each IC ECG signal is also used to independently determine R-S complex information 320 (e.g., ratio of R wave to S wave amplitude) and fractionation information 322 (e.g., slope information, information indicating an incidence of source behavior presented as the earliest activation from one of a plurality of electrodes, such as showing a percentage that the associated electrode was activated earlier than neighbouring electrodes) of the IC ECG signals and CV Block information 326 (e.g., information indicating slowed or blocked conduction (i.e., progression) of electrical impulses through the heart, such as the conduction time (CT) for the electrical pulse to travel a distance in the heart, the path length (i.e., the distance) and the CV of the electrical pulse).

As shown, a driver map 328 is generated from the cycle information 318, the earliness information 324 and the R-S complex information 320. A perpetuator map 330 is generated from the CV block information 326 and the fractionation information 322. As shown, the information used to generate the driver map 328 and the information used to generate the perpetuator map 330 are combined (e.g., a single map, overlaid maps or adjacent maps in one display area) to generate a combined driver/perpetuator map 334. The combined driver/perpetuator map 334 may then be used (e.g., interpolated as part of an exemplary map interpolation layer) to determine one or more ablation ROIs 350.

With regard to the AF Process 316 shown in FIG. 3B, the one or more detected LATs are used to independently generate activation/wave maps 336, CV maps 338 (e.g., maps generated from the CT, the path length and/or the CV of the electrical pulse) and block maps 344 (e.g., maps generated from information indicating a block in the conduction of the signal).

Activation/wave maps 336 may, for example, include a map representing an incidence of source behavior presenting the earliest activation of one of a plurality of electrodes restricted by the same wave, such as indicating a percentage of activation waves detected by a corresponding electrode activated earlier than neighboring electrodes though restricted by neighbors activated by the same wave. Activation/wave maps 336 may, for example, also include a map representing the incidence of electrode positions associated with a fibrillation wave start.

Each IC ECG signal is used to independently generate voltage maps 342 and fraction maps 340. The information used to generate maps 336-344 is combined to provide combined maps or video 346. In some embodiments, the information used to generate the activation/wave maps 336 and voltage maps 342 is combined to generate a combined activation/wave/voltage map or video and the information used to generate the CV maps 338, the block maps 344 and the fraction maps 340 are combined to generate a combined CV/block/fraction map or video. The combined maps/video 346 are analyzed (e.g., interpreted by medical personnel as part of an exemplary map interpretation layer) at block 348 to determine ROIs to be ablated at block 350. The combined maps/video 346 represent a spatio-temporal manifestation of the AF process which can be easily visualized and interpreted, facilitating an efficient and accurate process for determination of ROIs for ablation. Determined ROIs may be represented (e.g., displayed), for example, by color, by 3-D contour on a 4-D map, by icons (e.g., dynamically changing icons), etc.

In some embodiments, both the combined driver/perpetuator map 334 and the combined maps/video 346 are used to determine ROIs for ablation 350. For example, the combined driver/perpetuator map 334 can be used to determine ROIs for ablation 350 without using (e.g., viewing, analyzing) the combined maps/video 346.

In some embodiments, the quality map 332 is also used in combination with the combined driver/perpetuator map 334 and/or the combined maps/video 346 to determine ROIs for ablation 350. The quality map 332 is used to determine the trustworthiness of the generated maps (e.g., driver map 328, perpetuator map 330 and driver/perpetuator map 334) related to AF substrate 314 and the generated maps (e.g., activation/wave maps 336, CV maps 338, fraction maps 340, voltage maps 342 and block maps 344) related to the AF process 316 parameters. If the quality of the quality map is low, the generated maps are less trusted and appointing an ablation ROI 350 must be regarded with an increase level of care (e.g., by a physician) compared to when the quality map indicates high quality signals (IC ECGs) as the basis for the generated maps.

In some embodiments, determining ROIs for ablation 350 includes appointing or selecting one or more ablation sites for use in determining one or more ROIs for ablation. For example, ablation sites may be appointed or selected from driver evidence and perpetuator evidence (e.g., determined from the driver map 328, the perpetuator map 330 or the combined driver/perpetuator map 324) and ablation ROIs 350 may be determined based on the appointed sites.

The maps and mapping techniques disclosed herein potentially: (i) reduce AF map analysis training time; (ii) reduce time to determine ROIs for ablation; (iii) facilitate efficient interpretation of AF maps; and (iv) increase ablation success rates for ablation aimed at isolation and extinguishing of drivers, path lengthening, slowing of re-entry circuits, fibrillatory conduction and fractionated potentials.

An inventive technique presented herein incorporates fractionation to efficiently determine accurate ROI to be targeted for ablation.

Figure 4:
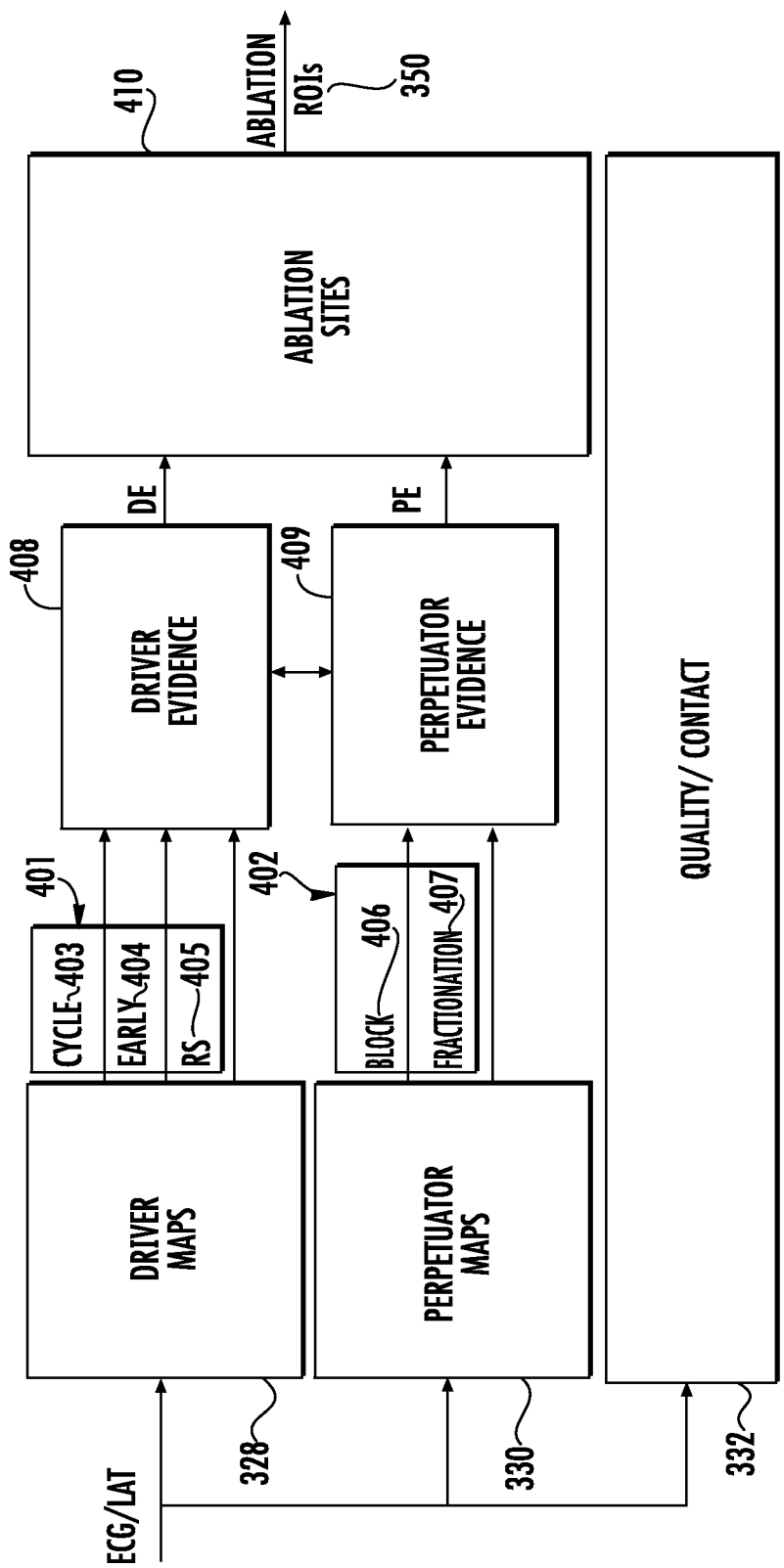
FIG. 4 illustrates mapping to appoint ROIs for ablation.

FIG. 4 shows a high level block schematic of the process of generating ablation ROIs (shown in FIG. 3B) based on driver maps 328 (cycle, early, RS) and perpetuator maps 330 (block and fractionation). From these driver and perpetuator maps 328, 330, driver and perpetuator related parameters 401, 402 are derived. Driver related parameters 401 include cycle length 403 (short cycle, fast repetition), earliness 404 (early activation driving the AF process), and RS ratio 405 (S-wave dominance). Perpetuator related parameters 402 include block 406 (block lines) and fractionated potentials 407 indicating non-uniform conduction. Both driver and perpetuator related parameters 401, 402 are further processed and combined into driver evidence 408 (De) and perpetuator evidence 409 (Pe). Finally, driver and perpetuator evidence 408, 409 are used (as two categories in Coumel's triangle of arrhythmogenicity) to derive potential ROIs for ablation 350, either acting as driver or perpetuator process, or both.

Figure 5:
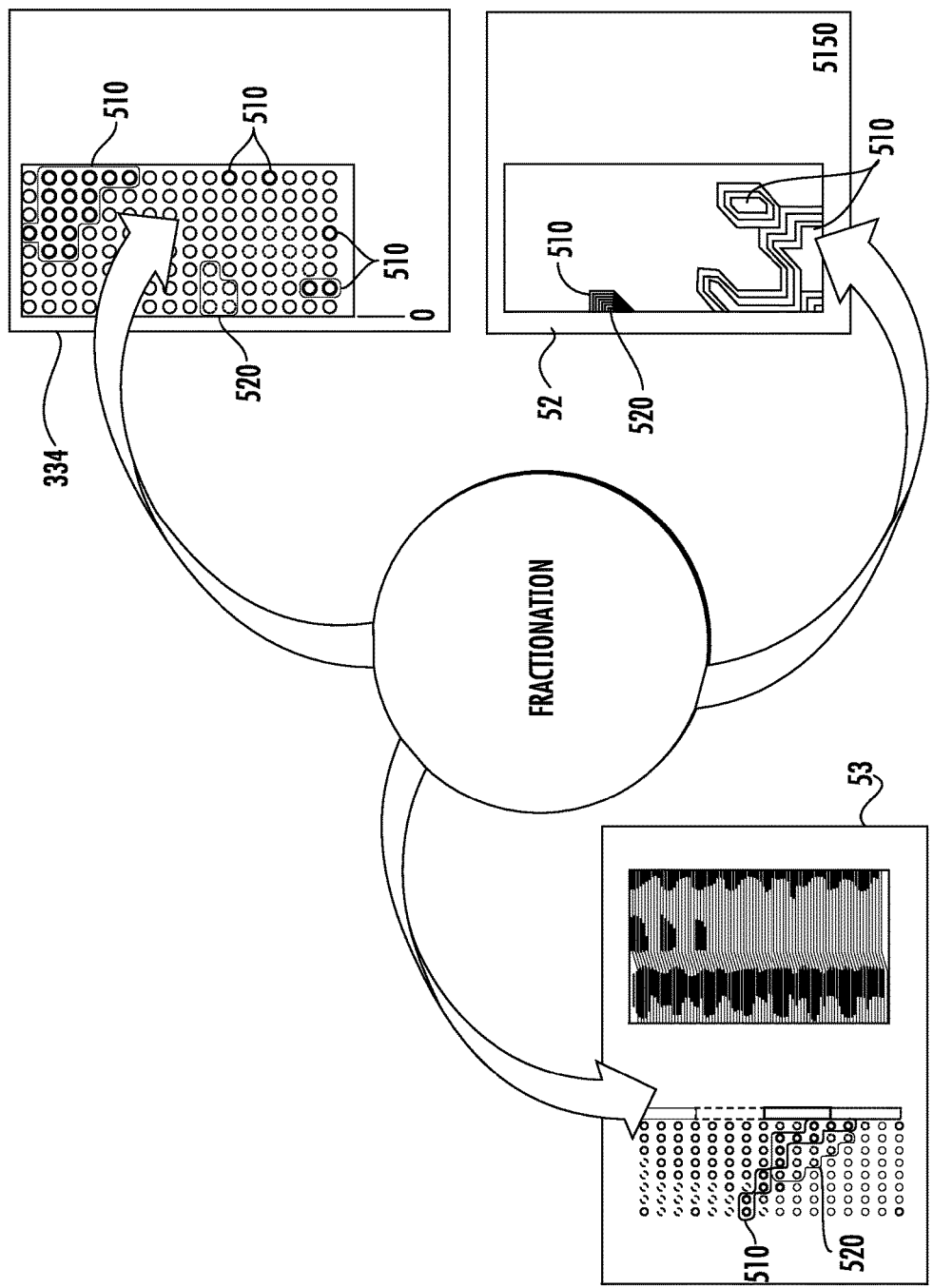
FIG. 5 is an overview of AF Mapping Fractionation.

FIG. 5 shows an example of a driver/perpetuator map 334 and temporal activation/fractionation maps (52, 53). The upper right panel in FIG. 5 is a driver/perpetuator map 334 where dots 510 represent example areas with increased driver evidence (De 408, as defined in FIG. 4) exceeding a predefined threshold, and dots 520 represent example areas of increased perpetuator evidence (Pe>T), (Pe 409, as defined in FIG. 4).

Figure 6:
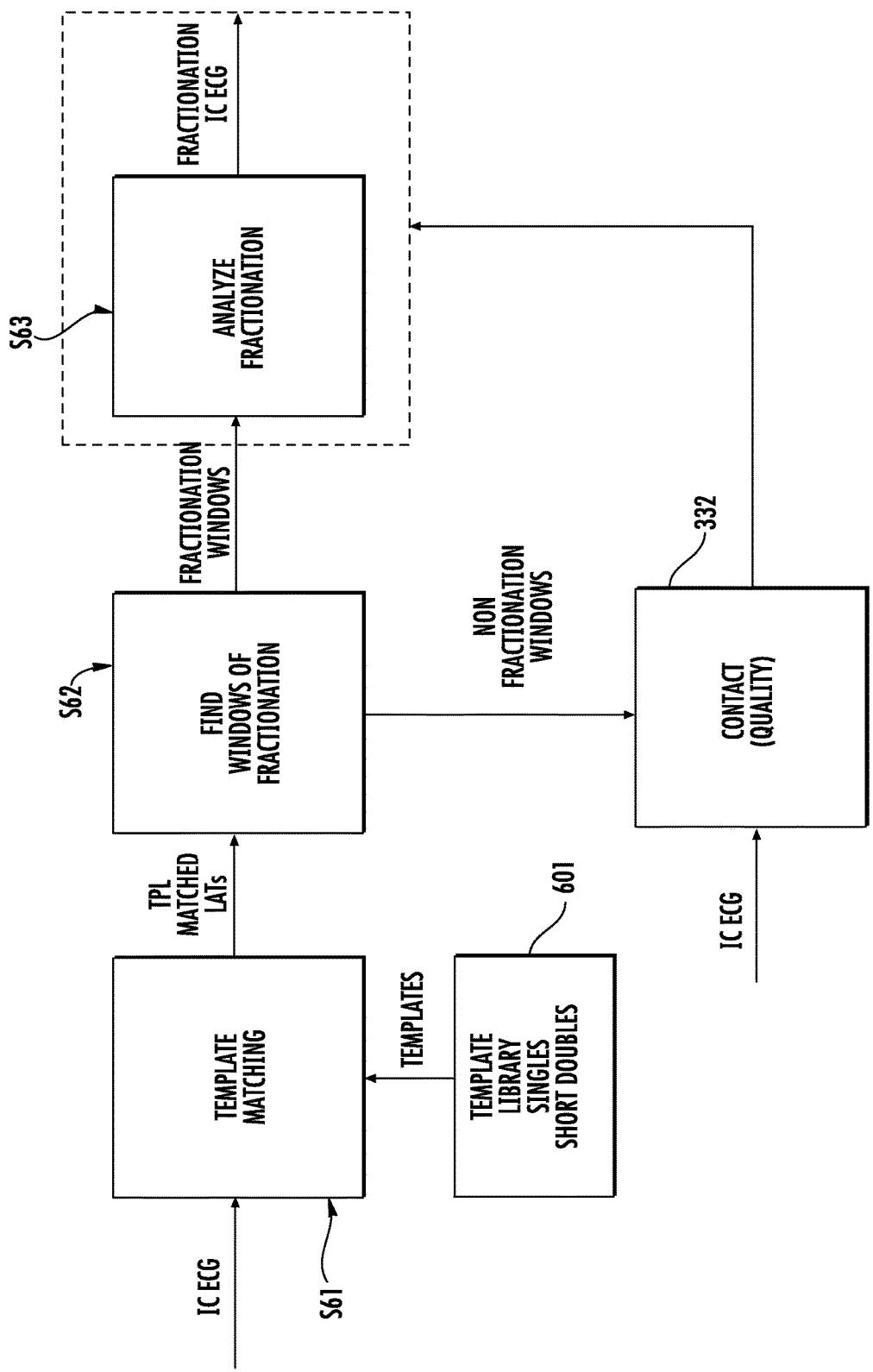
FIG. 6 is an overview of Fractionation Analysis in AF Mapping to Appoint ROIs for Ablation.

FIG. 6 provides an overview of the inventive technique as a flow diagram illustrating AF mapping to appoint ROIs for ablation using fractionation analysis. As shown in FIG. 6, in step S61, template matching is performed on an IC ECG, using templates from a template library 701 comprising synthetic singles and short doubles which are matched with an acquired IC ECG signal 302. The creation of the template library 601 will be described in greater detail below with reference FIGS. 7-10.

In step S62, windows of fractionation are found using the template matched LATs from step S61. This is discussed in detail below, see FIGS. 11 and 12. Note that non-fractionation windows are not analyzed and are considered for contact 332 or quality analysis.

In step S63, fractionation is analyzed and fractionated IC ECG is produced using windows of fractionation, and also using non-fractionation windows as contact. One embodiment of this analysis will be described in greater detail hereinafter with reference to FIG. 13.

Detection of fractionation is based on a filtering step, detecting and removing non-fractionated IC ECG potentials, including single, short double and long double potentials. FIGS. 7-11 illustrate AF mapping to appoint ablation ROIs showing detection of fractionated IC ECG.

Figure 7:
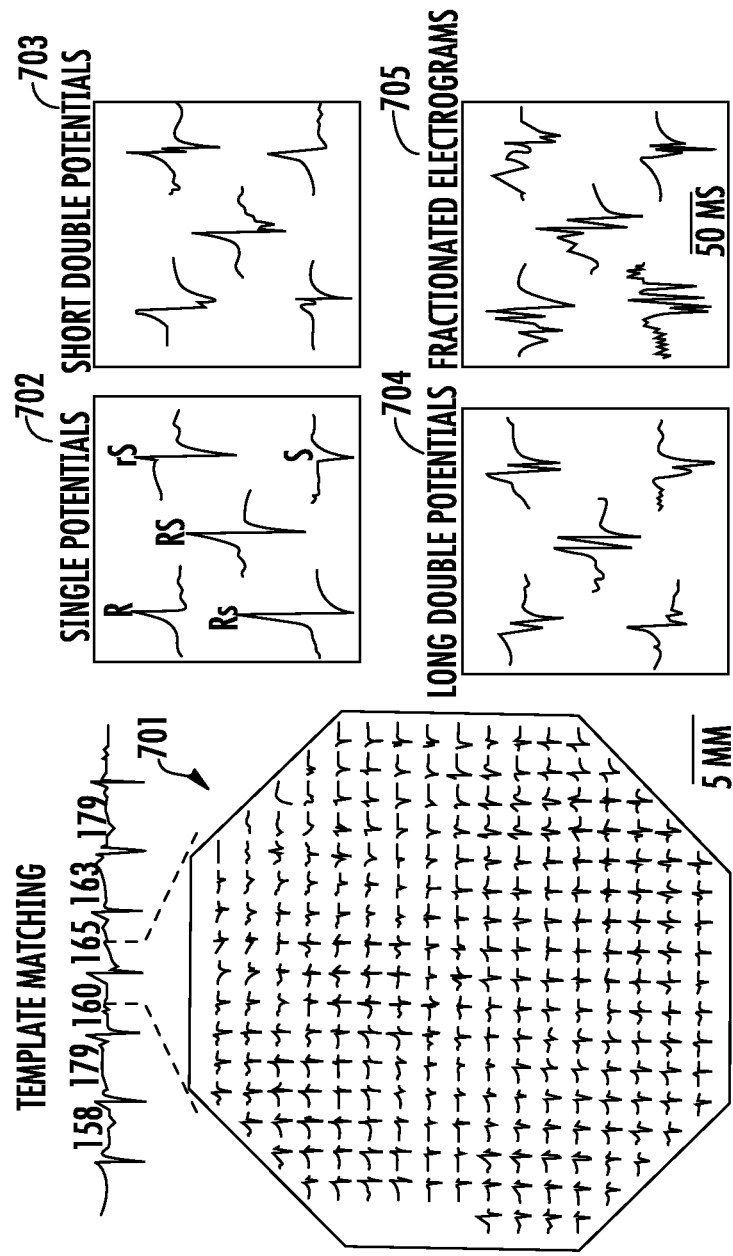

FIG. 7 shows the distribution and exemplars 701 of various types of electrograms acquired from one of a number of electrodes in contact with different areas of the heart (see FIG. 3A, block 302). These may include single potentials 702, short double potentials 703, long double potentials 704 and fractionated electrograms 705. All of the exemplars 701 are used as a basis for the creation of a template library 601 of synthetic single and short double potentials 801, 802.

In FIG. 8, synthetic single potentials 801 are defined by six characteristic points 81 (e.g., the filled circles shown in the lower left side of FIG. 8) connected by piecewise cubic spline interpolation 82 and bandwidth reduction (<250 Hz). In one embodiment, nine ratios between R- and S-wave amplitudes (from R to RS to S wave) are created as the synthetic single potentials 83. In one embodiment, the different synthetic single potentials 83 are created by varying amplitude (A), duration (milliseconds) and further performing bandwidth reduction, such as a low pass filter (LPF) cut off of 250 Hz. This is described in more detail below. As shown in the circle 85 on the right of FIG. 8, the synthetic potentials 83 can be overlaid on matching acquired single potentials 702. As is shown, there is not necessarily a match for each synthetic potential.

Figure 9:
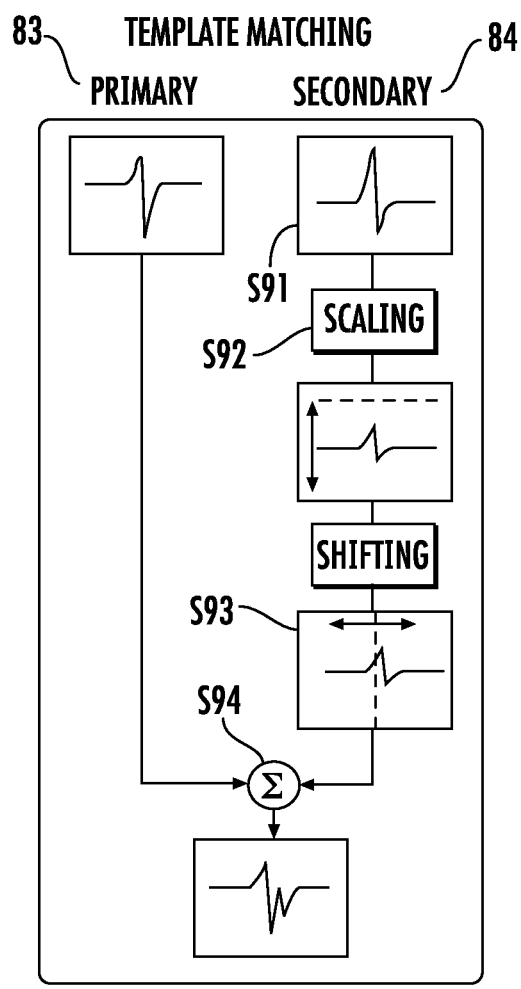

FIG. 9 provides additional detail regarding template matching with respect to creating synthetic double potentials, such that selections of two synthetic potentials (primary potential 83 and secondary potential 84) are used to create synthetic short double potentials. While the primary potential 83 is kept unchanged, the secondary potential 84 can be both scaled in amplitude (A) and time shifted (t) before addition with the primary potential 83 to create the short double potential. As shown in FIG. 9, initially, to create a synthetic set of short double potential templates, all combinations of two single potentials are selected (S91). The primary potential 83 components may be used without further manipulation. For the secondary potential 84 components, the following actions may be performed. Amplitude scaling of the secondary component (S92) is first performed. Next, a time shift (S93) is made with respect to relative time delay of the secondary component passing the recording electrode. Finally, the weighted and delayed singles, primary and secondary components, are summed (S94) to generate an entry in the set of 8,748 templates. In one embodiment, the template library specifications may include permutations of two templates from the set of single potentials, such that nine ratios are created, e.g., R, Rs, RS, fS, S, etc. In one embodiment, amplitude scaling, (e.g, zero (0) or fifty (50) percent amplitude reduction), may be used. In one embodiment, the secondary component time shift may be any of 4, 8, 12 16 ms as an example.

Figure 10:
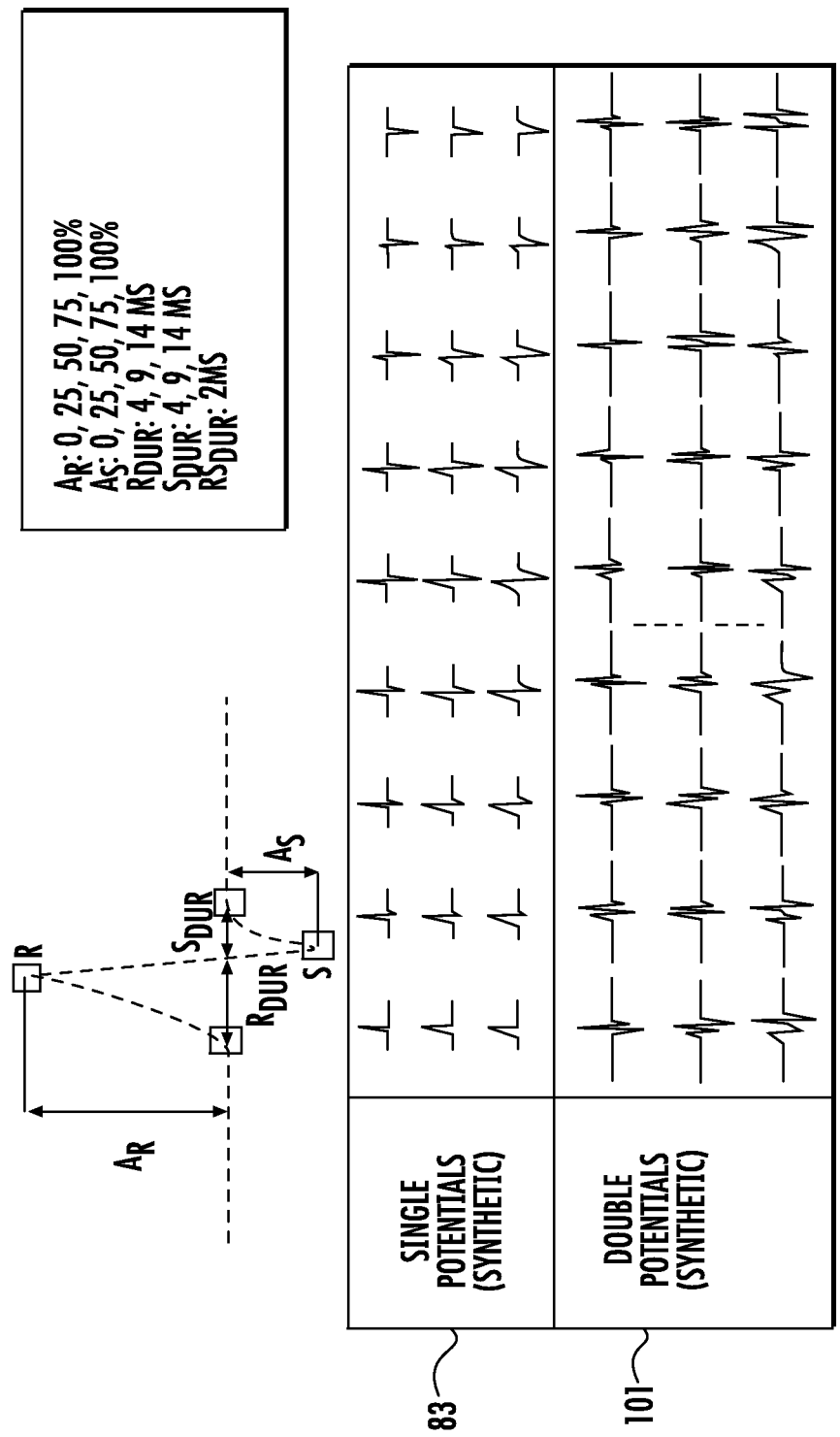

FIG. 10 shows a library of synthetic single potentials 83 and short double potentials 101 created using the amplitude $(A_R, A_S)$ 0, 25, 50, 75 and 100%, durations $(R_{Dur}, S_{Dur})$ 4, 9, 15 ms and $RS_{Dur}$ 2 ms parameters. As shown, twenty-seven single potentials 83 are created by varying the amplitude and then varying the duration; for example one single potential has $A_R=0$, $A_S=0$, $R_{Dur}=4$ ms, a second single potential has $A_R=25\%$, $A_S=0$, $R_{Dur}=9$ ms, another single potential has $A_R=50\%$, $A_S=0$, $R_{Dur}=14$ ms, yet another single potential has $A_R=75\%$, $A_S=0$, $R_{Dur}=4$ ms, etc. These synthetic single and double potentials 83, 101 are saved in the template library and used for the template matching portion of fractionation analysis.

Figure 11:
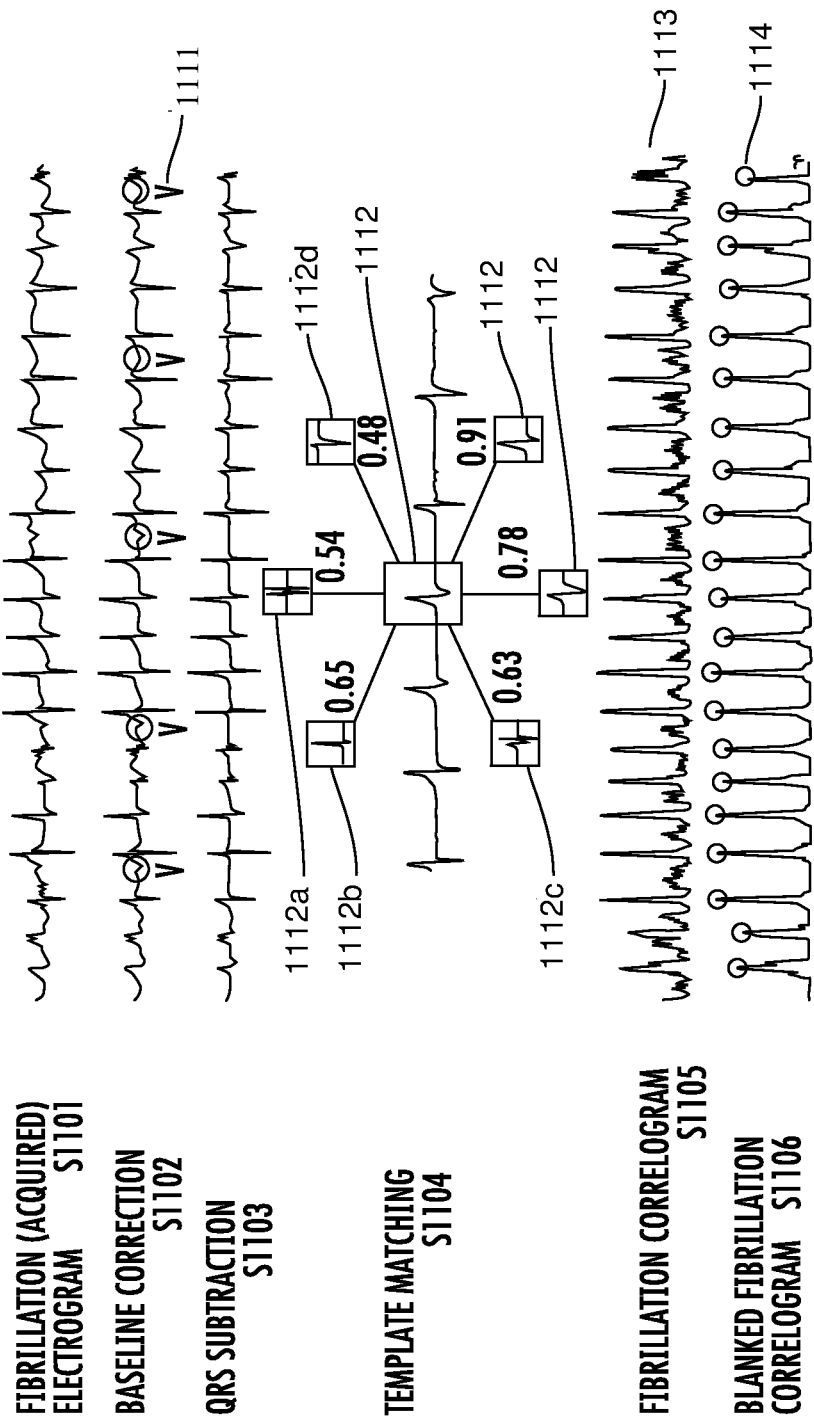

FIG. 11 shows a method of template matching including a template library specification for a library of synthetic single potential 83 and short double potentials 84. Initially, a fibrillation electrogram (IC ECG) is acquired (S1101). Next, a baseline correction is performed (S1102) in which the ventricular far field artifact 1111 is acquired. Next, QRS subtraction is performed (S1103), removing the ventricular far field artifact, and creating a simplified ECG. Next, template matching is performed on the simplified ECG as follows. A window of analysis is created and moved over the simplified ECG. FIG. 11 shows the window 1112 in the center of the simplified ECG, and also shows six "template-matching" templates, illustrating the templates from the template library being applied. As shown, the first template 1112a has a level of resemblance of 0.54 (approximately 54%). The second template 112b has a level of resemblance of 0.65 (approximately 65%). The third template 1112c has a level of resemblance of 0.63 (approximately 63%). The fourth template 1112d has 0.48 (approximately 48%), the fifth template 1112e has 0.91 (approximately 91%) and the sixth template 1112f has 0.78 (approximately 78%). Accordingly the window 1112 shows the "best match" of a level of resemblance of 0.91.

After the template matching has been performed, a fibrillation correlogram 1113 can be produced (S1105) using the "best match" template, e.g., 0.91 level of resemblance. This fibrillation correlogram 1113 can be created by calculating the correlation of the best fitting template (e.g., maximum correlation). Finally, the fibrillation correlogram 1113 is blanked for correlations less than a predefined maximum threshold (S1106), e.g., a threshold less than 0.4 or 0.5. Further, the blanked fibrillation correlogram 1113 shown in FIG. 11 includes a template number and detection point for each peak 1114.

Figure 12:
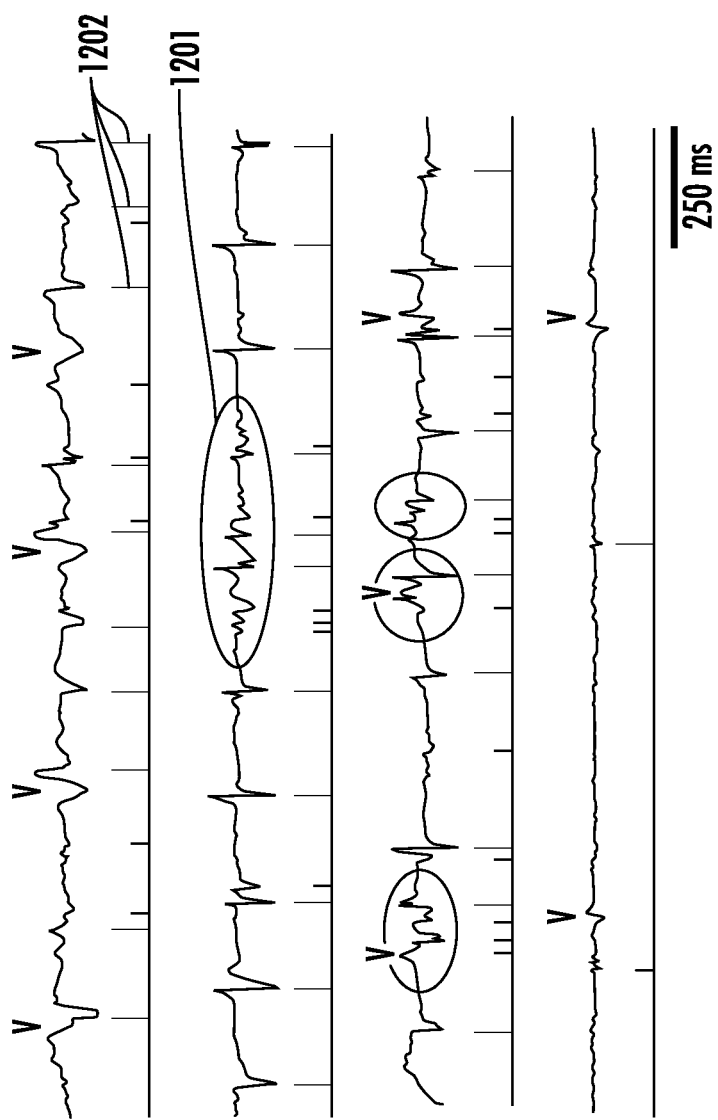
FIG. 12 illustrates AF Mapping to Appoint Ablation ROIs Detect Fractionated IC ECG.

FIG. 12 shows a graph illustrating detection of a fractionated IC ECG. Fractionation episode detection can be performed using template matching to exclude single and short double potentials. For example, the detection process finds areas such as 1201 (row 2, indicated in the elliptical) where no match is detected. These non-matching areas 1201 are special and of interest when determining ablation ROIs 350. Fractionation analysis may be aimed at identification of perpetuating areas during AF. Accordingly, combining fractionation and block can determine a perpetuator, shown as short lines 1202 (top row) in FIG. 12.

Figure 13:
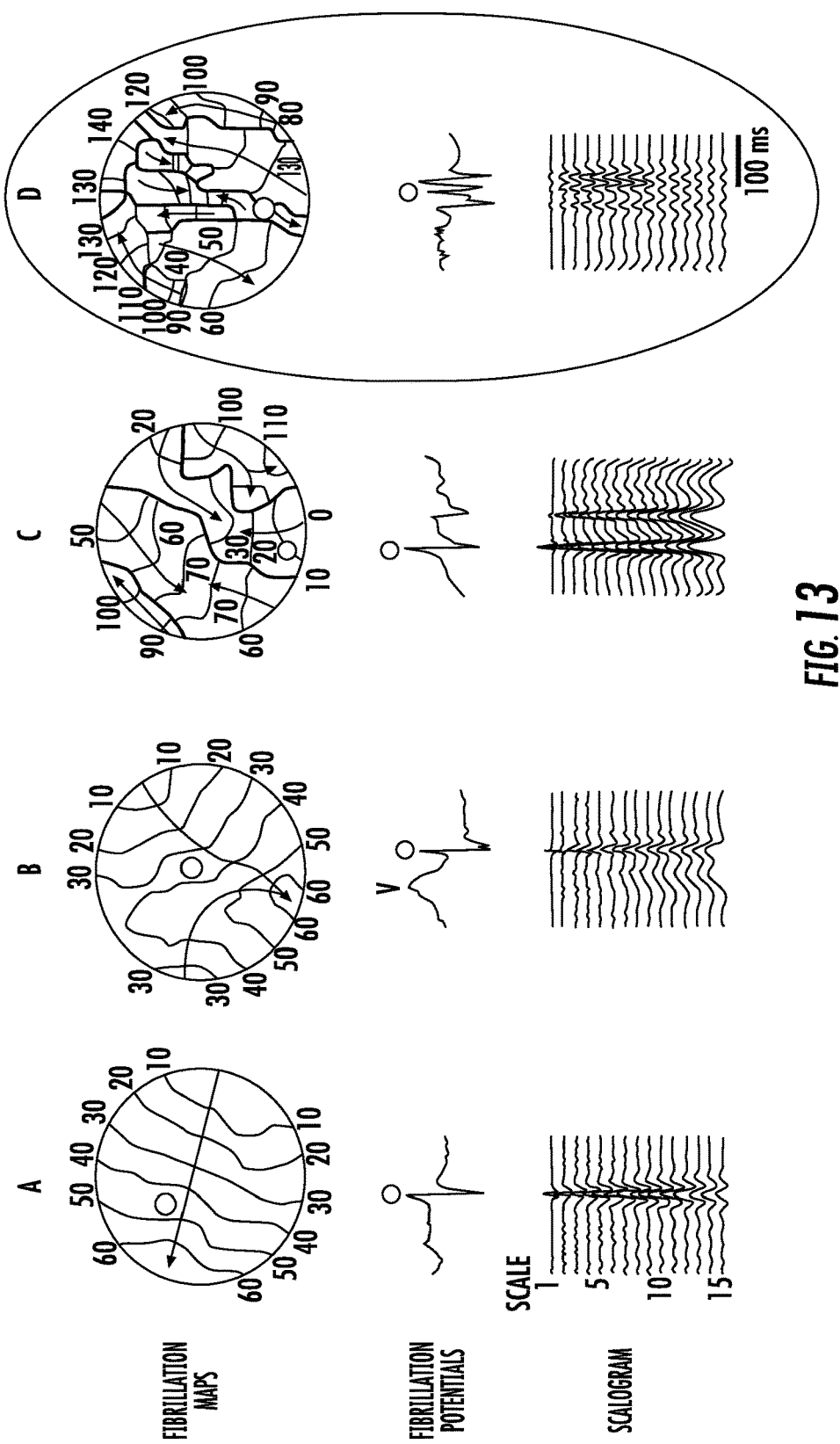
FIG. 13 illustrates AF Mapping to Appoint ROIs for Ablation.

FIG. 13 shows a graph illustrating different examples of AF mapping to appoint ROIs for ablation. The fibrillation maps (top row), fibrillation potentials (center row) and a scalogram (bottom row) resulting from wavelet decomposition of fibrillation potentials are shown in FIG. 13. Example D displays multiple dissociated waves, epi-endo dissociation, and slow and/or staggered conduction which are used as tools or evidence to locate areas of fractionation.

Figure 14:
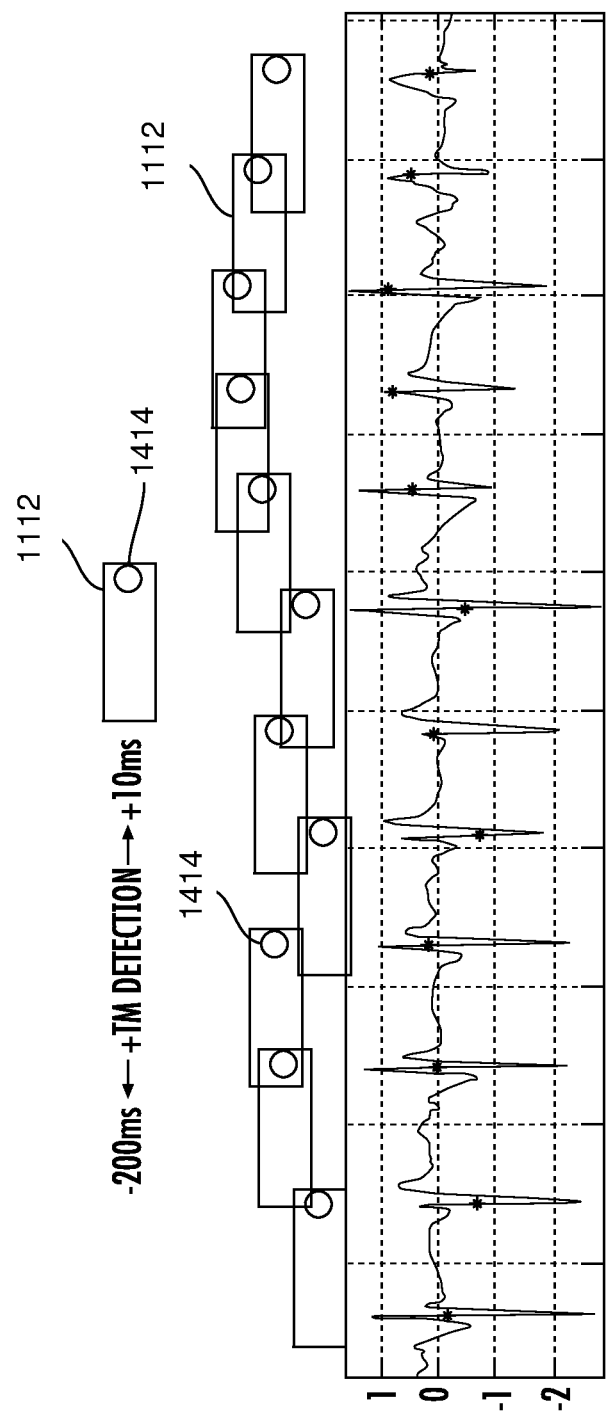
FIG. 14 illustrates AF Mapping Detect Fractionated Episodes in IC ECG.

FIG. 14 shows AF mapping to detect fractionated episodes in an IC ECG. As shown in FIG. 14, multiple windows 1112 (−200 ms←+TM detection→+10 ms) are created around each detection point 1414 that result from template matching (i.e. TM detection). As long as subsequent windows overlap, no fractionation is detected. When a non-overlapping window has been detected, the fractionation signal is set to zero.

Figure 15:
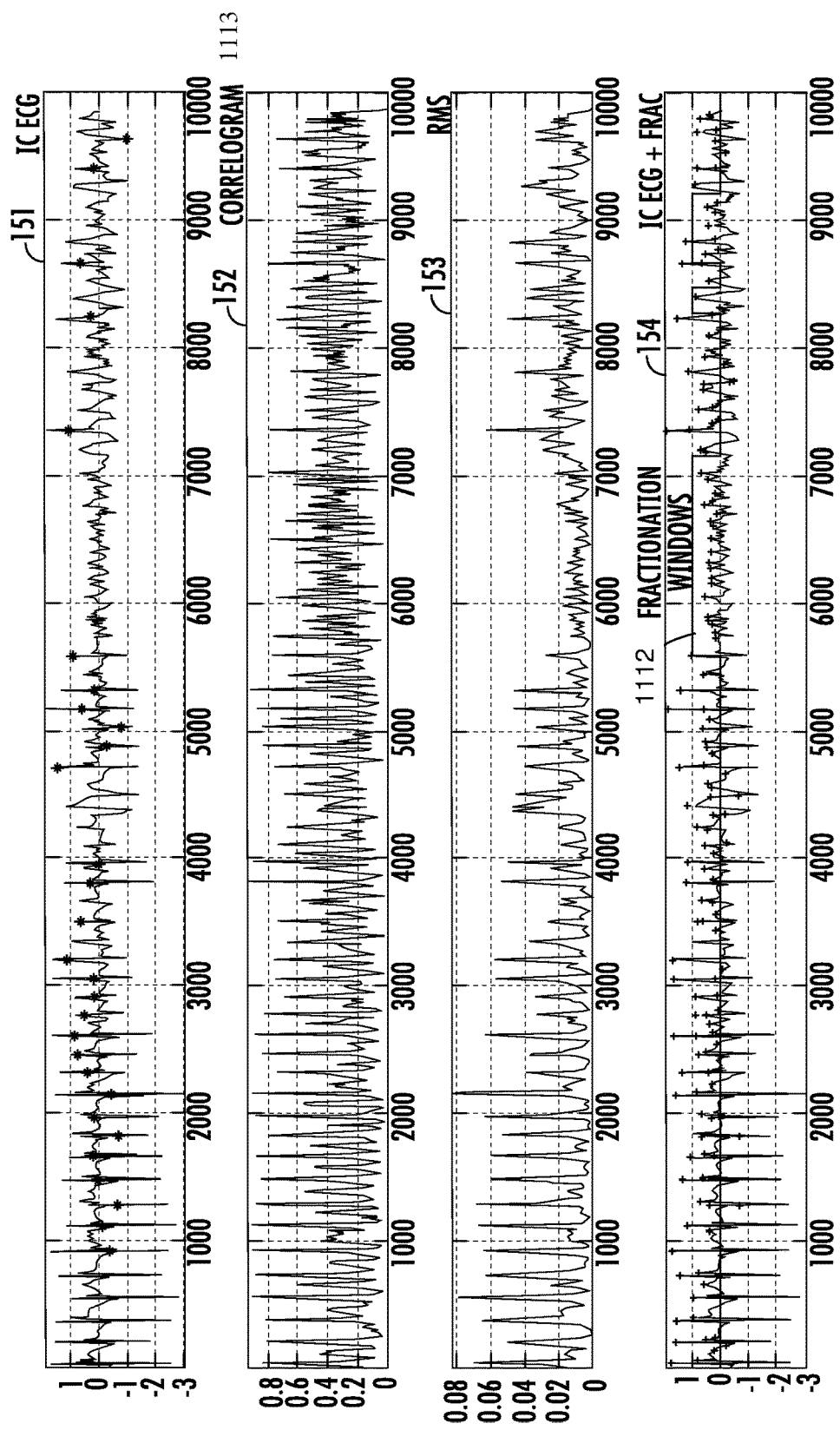
FIG. 15 illustrates AF Mapping Detect Fractionated Episodes in IC ECG.
Figure 16:
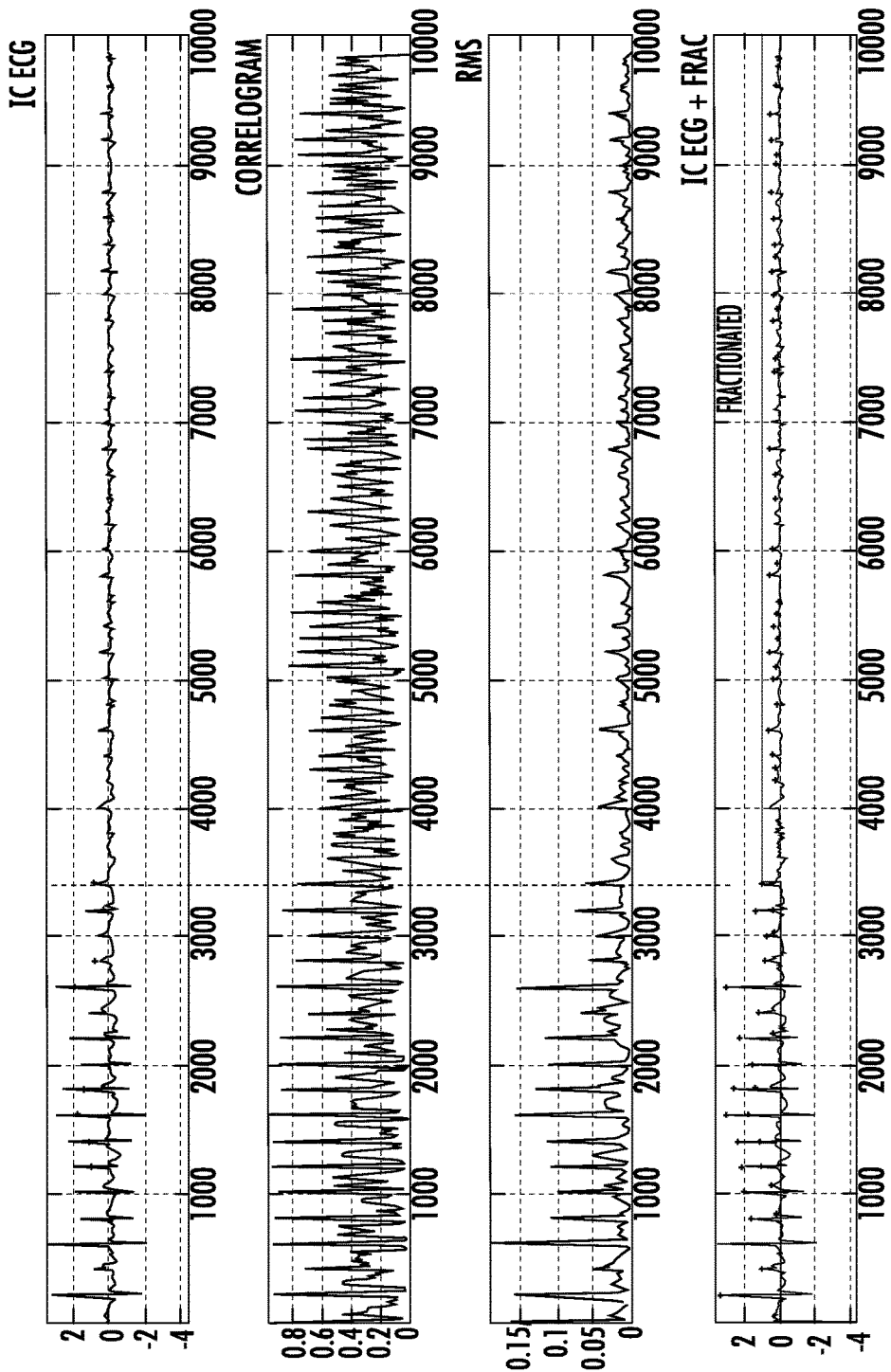
FIGS. 16-17 illustrate AF Mapping Detect Fractionated Episodes in IC ECG.

FIGS. 15 and 16 show examples of AF mapping to detect fractionated episodes in an IC ECG. The top graph (IC ECG) 151 shows an acquired ECG. The next graph 152 shows a correlogram 1113 derived in accordance with the procedure described above with respect to FIG. 11. The next graph 153 shows root mean square (RMS) amplitude processing. The bottom graph 154 illustrates alternating episodes of non-fractionated and fractionated episodes; (i.e. fractionation windows 1112). In other words, the bottom graph 154 indicates fractionated elements of the ECG signal Referring to FIG. 16, this shows a non-fractionated IC ECG followed by a fractionated IC ECG. The vertical dotted line shows the transition from a non-fractionated to fractionated IC ECG. In this manner, this change can be clearly observed in the IC ECG.

Figure 17:
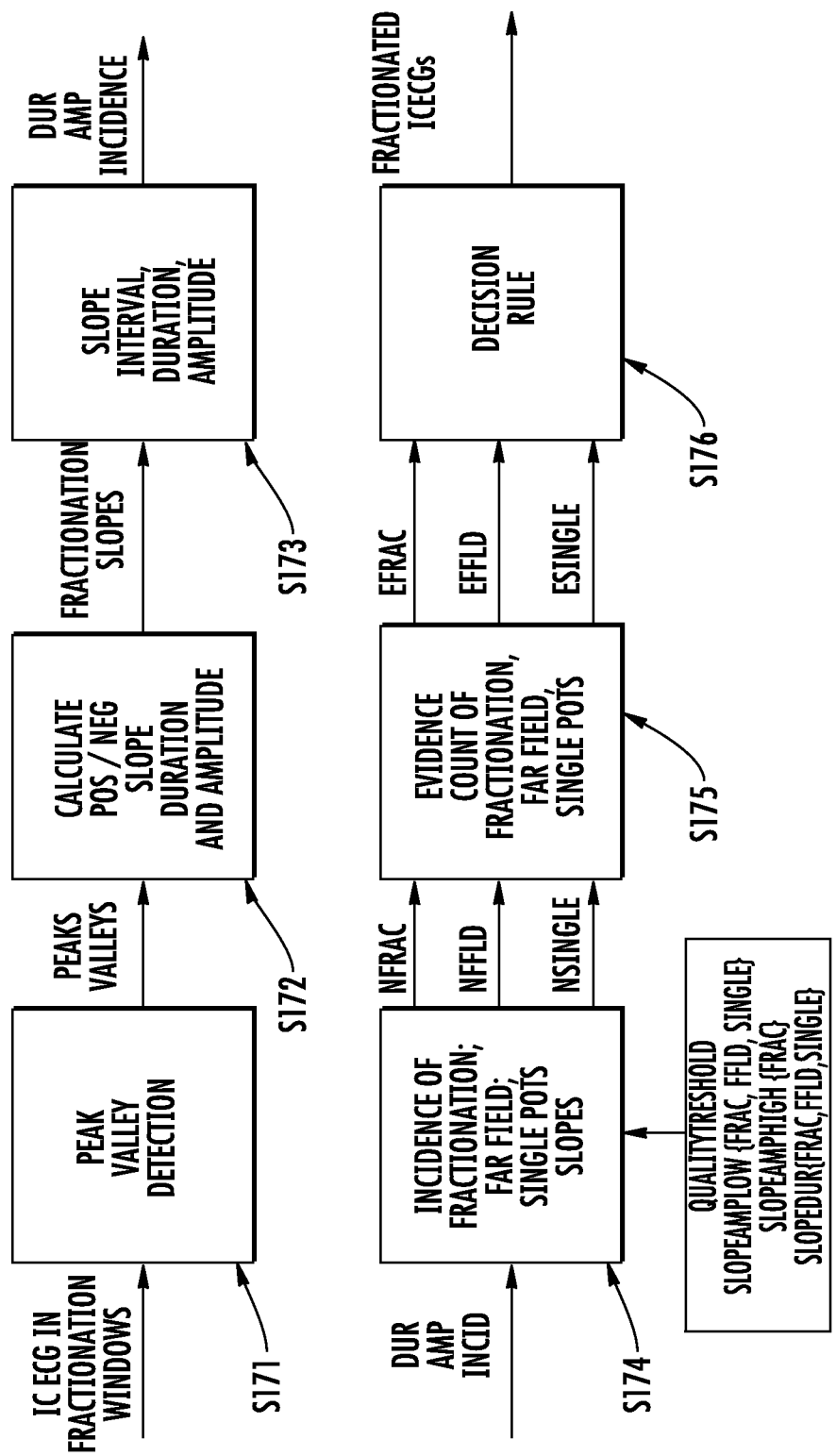

FIG. 17 is a more detailed flow diagram of a method for AF mapping to detect fractionated episodes in one embodiment using slope analysis. IC ECG fractionation windows are input and peak valley detection is performed (S171). Peak valleys are output and then positive/negative slope duration and amplitude are calculated (S172). Fractionation slopes are output from step S172 and slope interval, duration and amplitude are used to calculate duration, amplitude and incidence (S173).

Duration, amplitude and incidence are then used to calculate the number of fractionation (NFRAC), far field (NFFLD) and single potential slopes (NSINGLE) (S174). NFRAC, NFFLD and NSINGLE are output from step S174 into step S175. In step S175, evidence count of fractionation (EFRAC), far field (EFFLD), and single potentials (ESINGLE) are calculated. EFRAC, EFFLD and ESINGLE are output from step S175 and input into step S176. In step S176, a decision rule is implemented and the fractionated IC ECGs are output. In one embodiment, a fractionated IC ECG may be identified if EFRAC is greater than a high predetermined threshold such as 90%. In another embodiment, a fractionated IC ECG may be identified if EFRAC is greater than another, lower predetermined threshold, such as 70%, and both EFFLD and ESINGLE are less than a third, low predetermined threshold.

In yet another embodiment, data such as a predetermined threshold (QUALITYTHRESHOLD), a low slope amplitude with parameters, e.g., SLOPEAMPLOW {frac,ffld, single}, a high slop amplitude with paramenters (SLOPEAMPHIGH {frac}), and/or a duration of slope with parameters (SLOPEDUR {frac,ffld,single}) can be input to step S174. In this embodiment, this data can be used to calculate the number or incidence of NFRAC, NFFLD, NSINGLE.

Fractionation maps can include two categories—amplitude and interval. A fractionation amplitude map illustrates incidence of electrode positions associated with a fractionated potentials. A fractionation interval map illustrates incidence of electrode positions associated with fractionated potentials.

Figure 18:
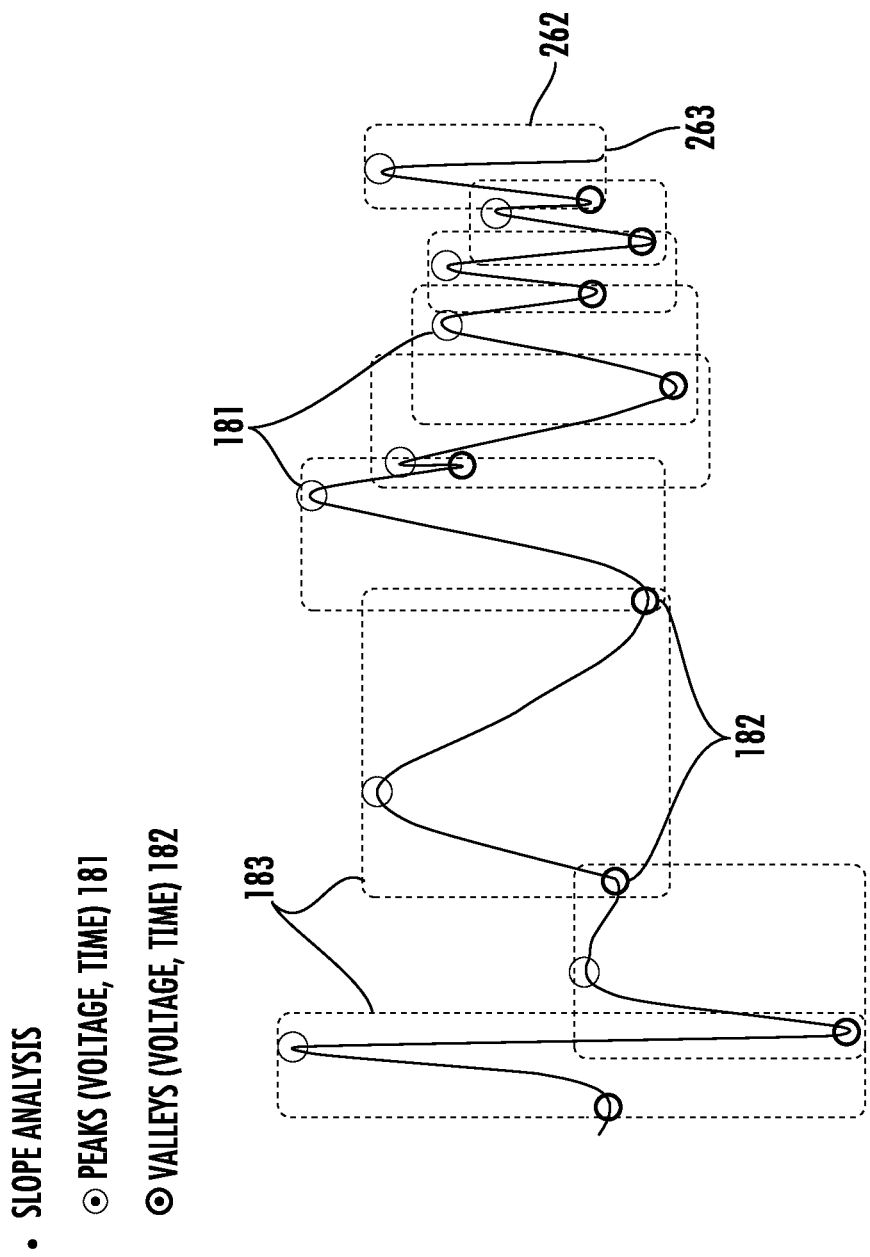
FIG. 18 illustrates AF Mapping Detect Fractionated Episodes with increased specificity.

FIG. 18 illustrates an embodiment of S171 of FIG. 17, that is, peak valley detection. As shown in FIG. 18, slope analysis can include displaying peaks 181 and valleys 182 of an acquired ECG 302. Each dotted-line rectangular box 183 comprises a "triplet" of slope values of valley 182, peak 181, and valley 182. Further, each rectangular box 183 has as its height 262 the amplitude of the slope, and as its width 263 the duration of the slope. This is further described with respect to FIG. 26.

Figure 19:
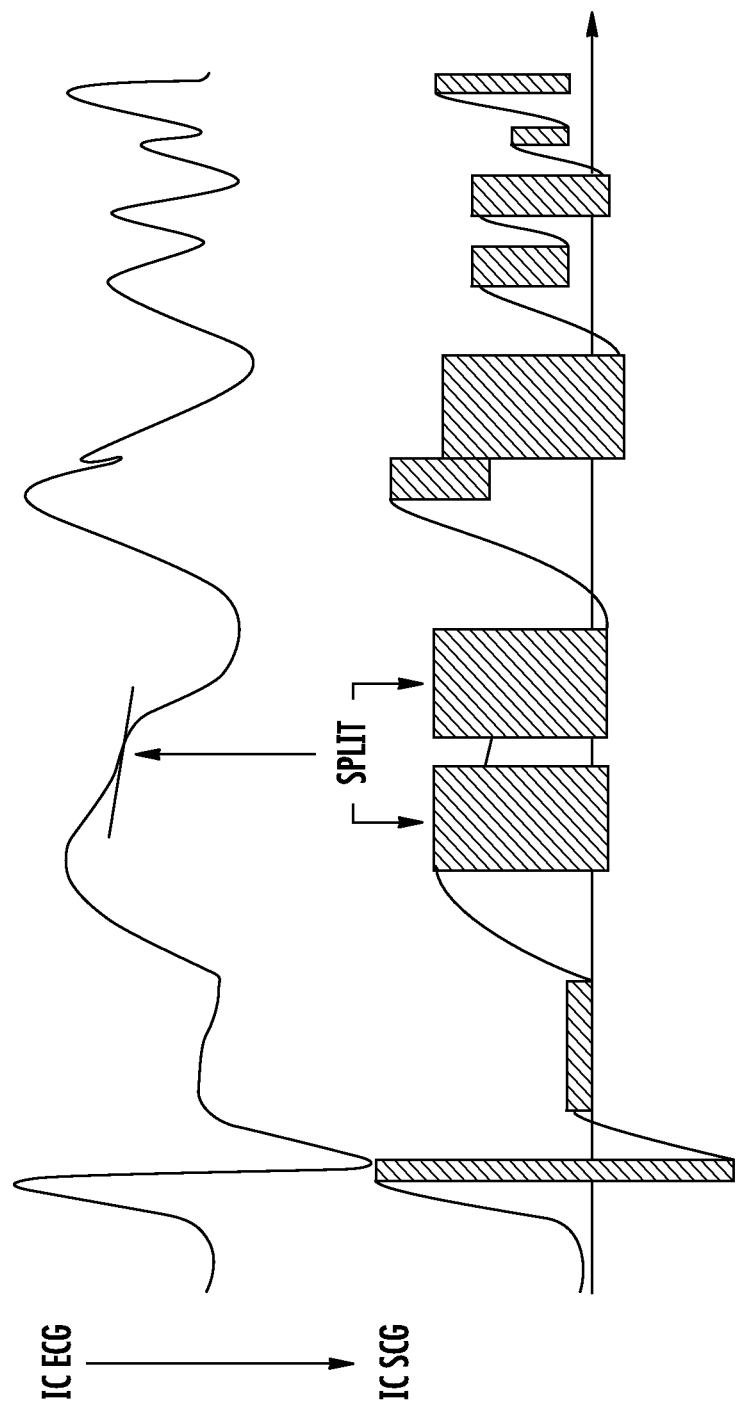
FIG. 19 illustrates AF Mapping Comprehensive Mapping.

FIG. 19 shows an embodiment of S172 and S173 regarding calculation of the positive/negative slope amplitude duration and amplitude. FIG. 26 shows the dotted-line rectangular boxes 183 of FIG. 18 as solid boxes 191. As in FIG. 18, the rectangular boxes of FIG. 19 indicate slope such that the height 262 of each box is the slope amplitude and the width 263 of each box is the slope duration. Note that for fractionation analysis, as discussed herein, downward slopes are of interest and upward slopes are generally ignored.

Figure 20:
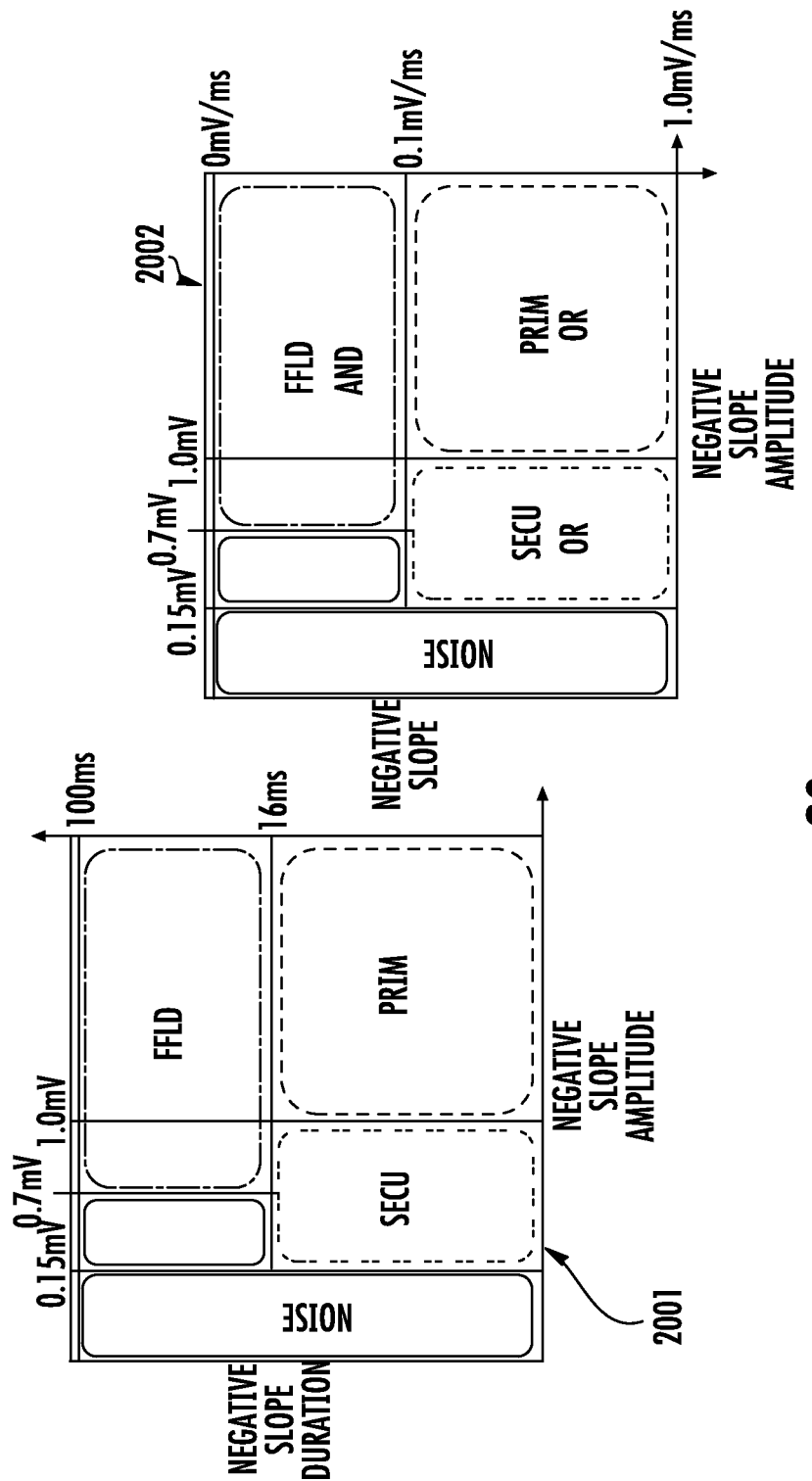
FIG. 20 illustrates AF Mapping Comprehensive Mapping—Slope View.

FIG. 20 is a diagram of an embodiment of S174 regarding classification of the slope characteristics wherein two decision rectangles are presented. These are decision rectangles indicating slope information. As shown, each of the two rectangles 2001, 2002, comprise smaller rectangles illustrating slope classes such as far field (FFLD), noise, primary (PRIM) and secondary (SECU) components. Slope parameter(s) thresholds are defined to position the rectangles, relating negative slope duration vs. amplitude 2001 and relating negative slope to negative slope amplitude 2002 to obtain a non-ambiguous selection of one of the slope classes. For example, the slope duration can range from 0 ms to 100 ms, as shown in rectangle 2001, while the slope can range from 0 to 1 mV/ms as shown in rectangle 2002. Slope characteristics are discussed in more detail below.

Figure 21:
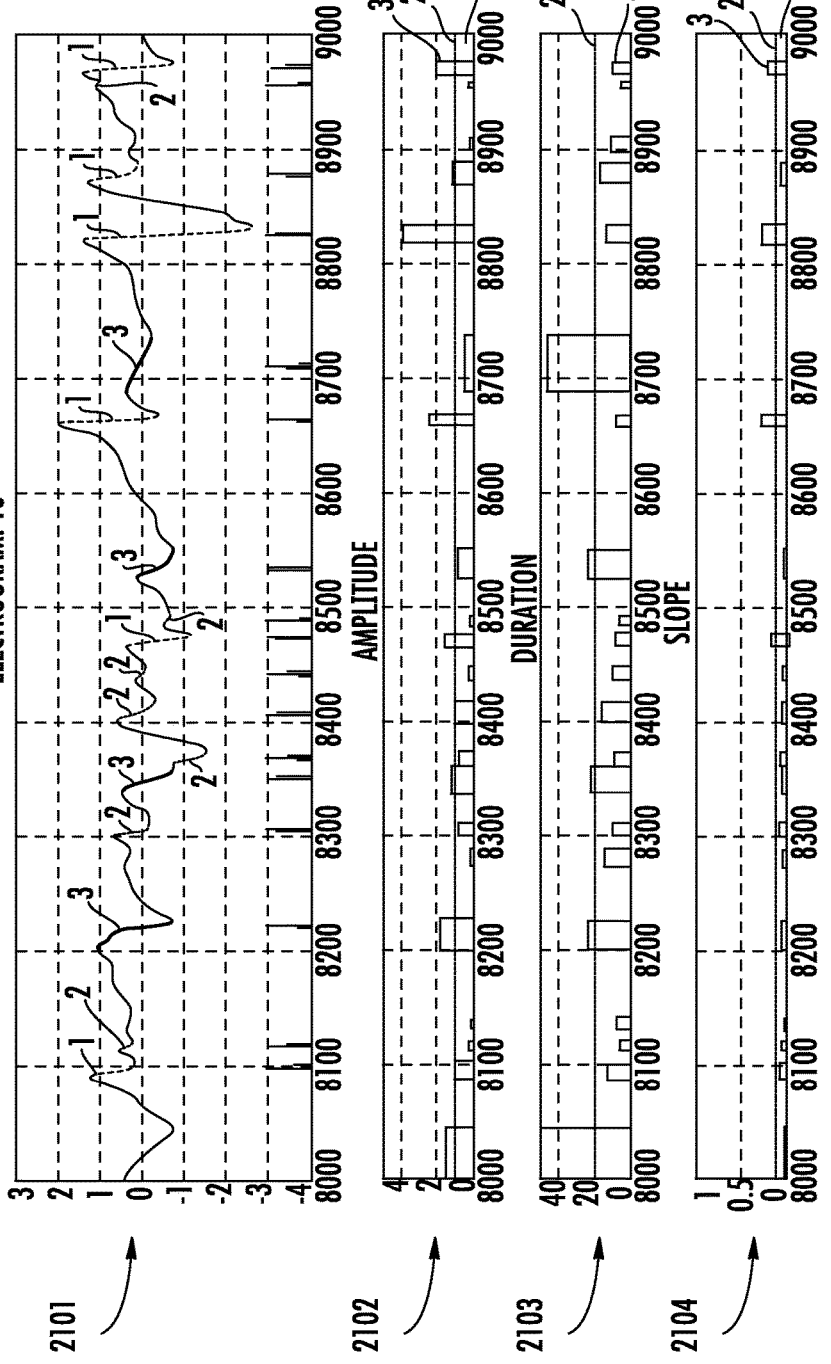
FIG. 21 illustrates AF Mapping Comprehensive Mapping—characterize slopes.

FIG. 21 shows four graphs. From top to bottom they are Electrograms 2101, Amplitudes 2102, Duration 2103 and Slope 2104. The upper graph 2101 shows the IC ECG and timing of slopes detected with their classification (PRIM, SECI or FFLD) based on the slope characteristics (slope amplitude, duration and slope) which are separately shown in the bottom three graphs 2102, 2103, 2104 along with their thresholds. The bottom graph 2104 illustrates the time stamp of the slope, (e.g. slope incidence). Each graph includes primary 1, secondary 2 and far field 3 slopes. This data is used to make decisions regarding the ECG and whether or not it includes fractionation, as discussed in more detail below.

Figure 22:
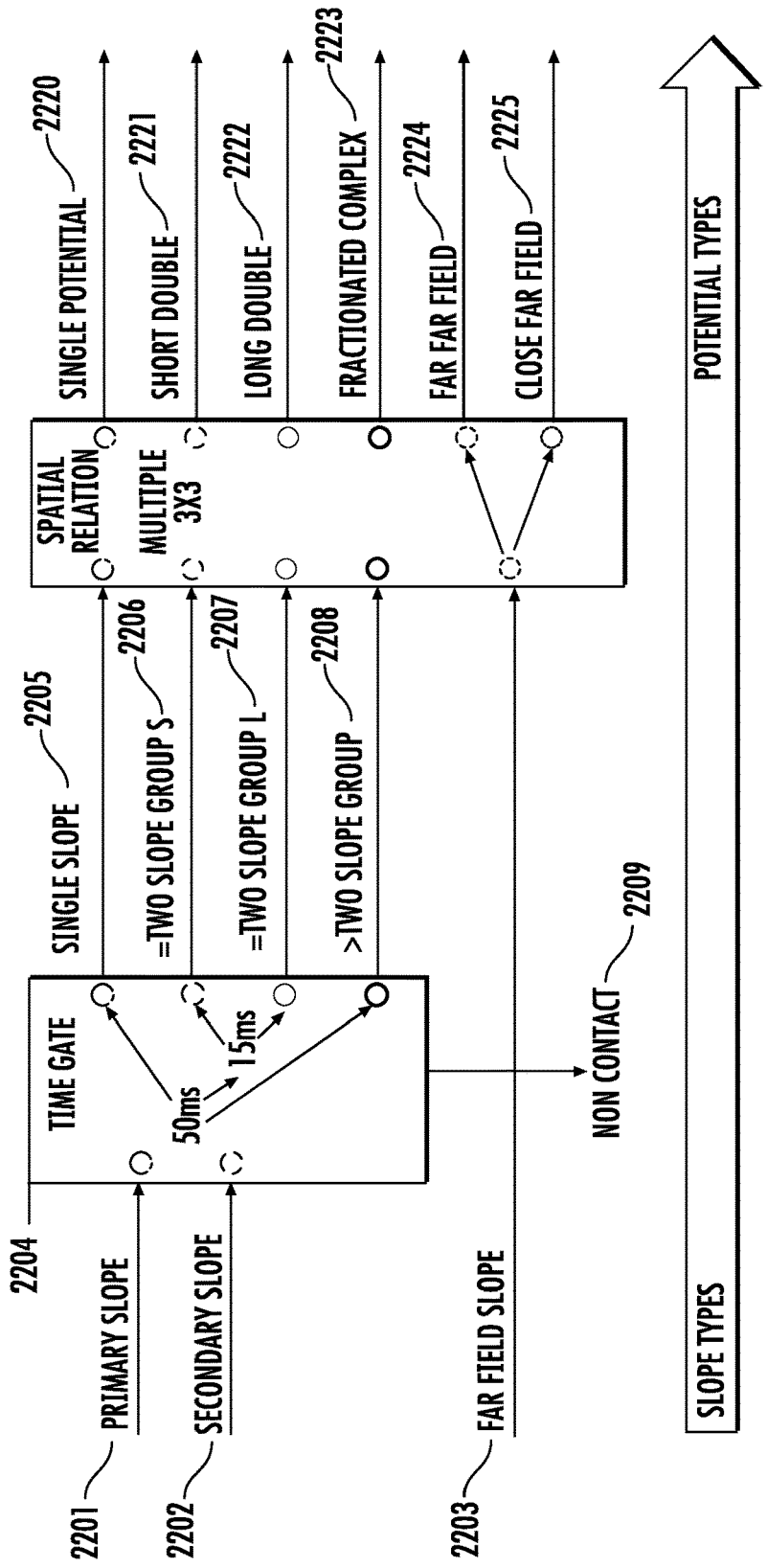
FIG. 22 shows a progression from slope types to potential types.

FIG. 22 shows a progression from slope types to potential types. In one embodiment, primary slope 2201, secondary slope 2202 and far field slope 2203 can progress to potential types of single potential 2220, short double potential 2221, long double potential 2222, fractionated complex 2223, far field 2224 and close far field 2225. The progression from primary slope 2201 and secondary slope 2202 is initially performed using a time gate 2204. The time gate 2204 processes slopes within time limits, which can be, for example, 15 ms and 50 ms as shown in FIG. 22. However, these durations are merely an example and other timings may be used. Both primary slopes 2201 and secondary slopes 2202 are input into the time gate 2204 and an initial determination is made for converting the slopes into potentials based on these time limits. Primary and secondary slopes having a time limit of 50 ms, for example, can become one of two slope groups: single slope 2205 or >two slope group 2208 based on whether the slopes are singular or grouped. Also, primary and secondary slopes 2201, 2202 having a time interval of 15 ms can be grouped into a long (>15 ms interval) group 2207 or a short group 2206 (<=15 ms interval), (e.g., two slope group S (short) 2206, or two slope group L (long) 2207. Groups with more than 2 slopes, and less than 50 ms intervals are grouped into the >Two slope group 2208. After processing in the time gate 2204, the slopes progress into potentials. As shown, single slopes are considered to have a special relation; they progress into single potentials 2220. Two slope group S 2206 are typically a 3×3 multiple, and progress into short double potentials 2221. Two slope group L 2227 progress into long double potentials 2222, and >Two slope group 2208 progress into fractionated complex potentials 2223 which, as discussed herein, are special and receive special review. The potentials are grouped into consecutive slopes with an interval less than 50 ms, and are analyzed as slope types per group of slopes. Those potentials not within the group are output as non-contact 2209 and receive no additional analysis. Typically the group size is (2, >2).

FIG. 23 further illustrates time gate and temporal grouping of primary and secondary slopes. As shown in FIG. 23, non-contact potentials produced by the time gate 2209 can be analyzed as follows. For the non-contact potentials, a 3×3 spatio-temporal time window is analyzed, and the FFLD slope annotation is performed. Evidence for non-contact is collected by searching the 3×3 neighborhood for far-field and additional non-contact potentials. Moreover, slope annotations within window (t+/−W) are analyzed for primary slopes. This analysis can reveal that either no primary slopes are found in center electrode IC ECG or that primary slopes are found in center electrode IC ECG. The finding of no primary slopes is based on the non-contact evidence and that only far field slopes are found in neighboring electrodes of the non-contact evidence, and further that primary slopes are found in neighboring electrodes of the non-contact evidence. The finding of primary slopes in center electrode IC ECG is based on far field potential evidence and synchronous primary slopes found in neighboring electrodes of the non-contact evidence.

Figure 24:
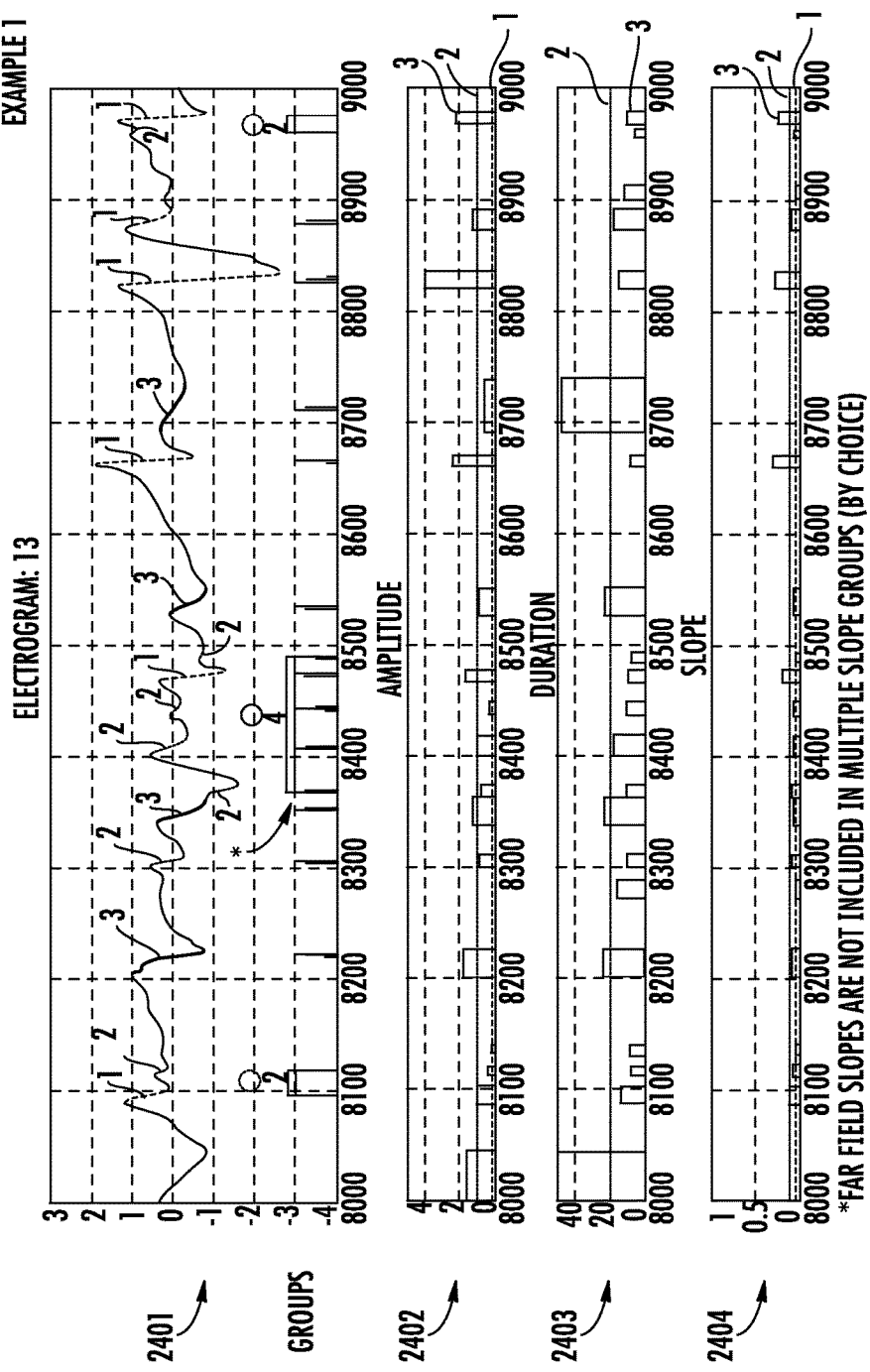
FIGS. 24 and 25 provide two examples of groupings, further illustrating single slope, two slope group, long double slope group and >two slopes.
Figure 25:
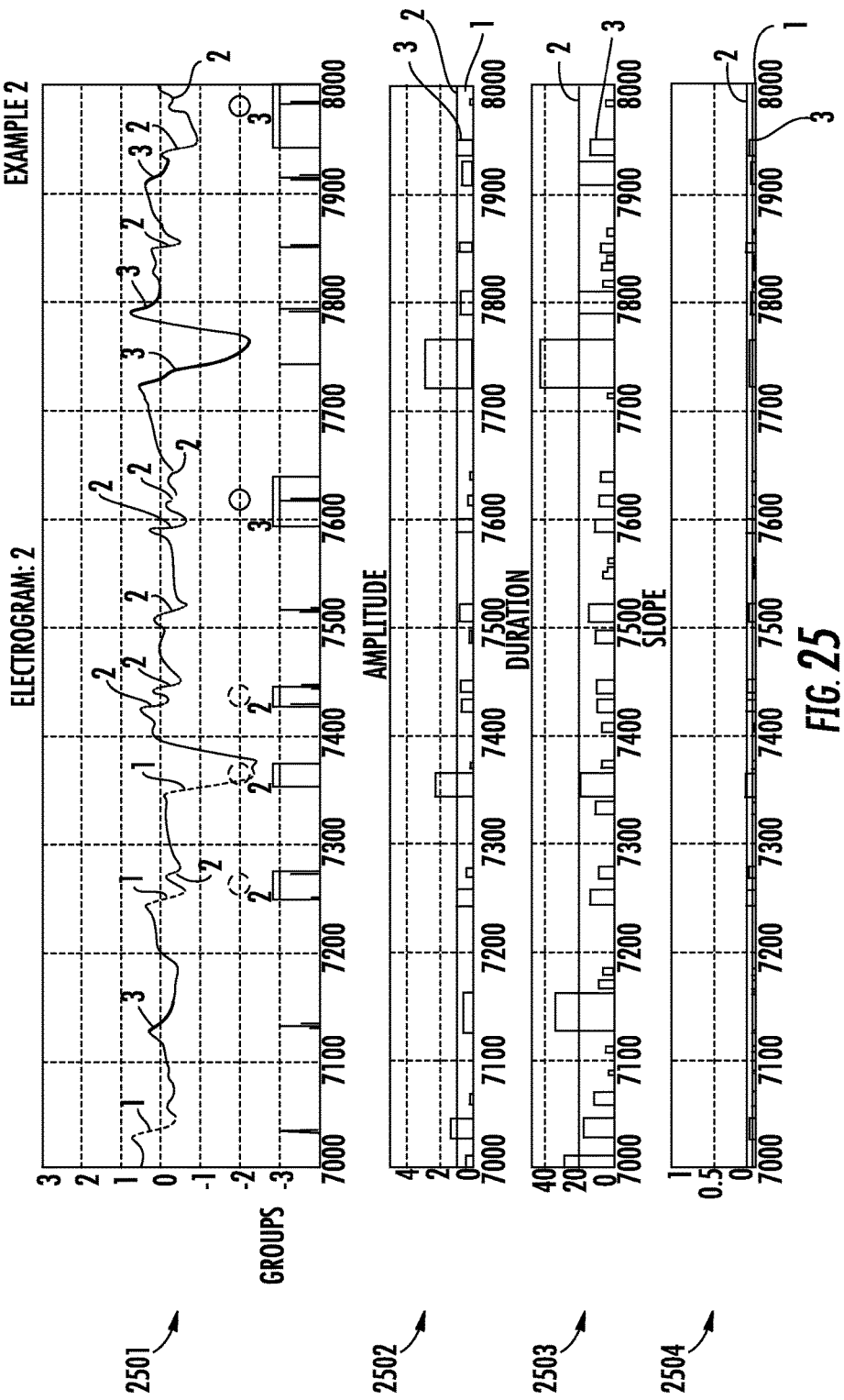

FIGS. 24 and 25 provide two examples of groupings, further illustrating single slope 2205, two slope group 2206, long double slope group 2207 and >two slopes 2208 (as defined above). These figures show graphs of electrograms 2401, 2501, amplitude 2402, 2502, duration 2403, 2503 and slope 2404, 2504, from top to bottom respectively. Each includes primary 1, secondary 2 and far field 3 slopes. FIGS. 24 and 25 further illustrate neighborhood groups which are discussed further below.

FIG. 26 illustrates the spatio-temporal analysis of identified slopes represented as rectangles. The matrix or set of circles on the left indicate the topological positions of eight (8) neighboring electrodes labeled 1-8 and C, i.e., center electrode. On the right of FIG. 26, a series of slope traces is shown. The top trace 261 shows the slopes of the center electrode C as rectangles represent the amplitude and duration of the slopes. As aforementioned, the amplitude 262 of the slope (A) is represented as height, and the duration 263 of the slope (D) is represented as width. The lower traces 1-8 show the same information for other eight (8) neighboring electrodes 1-8 that surround the center electrode C. For example, the output of electrodes 1 and 8 are shown in FIG. 26.

Figure 27:
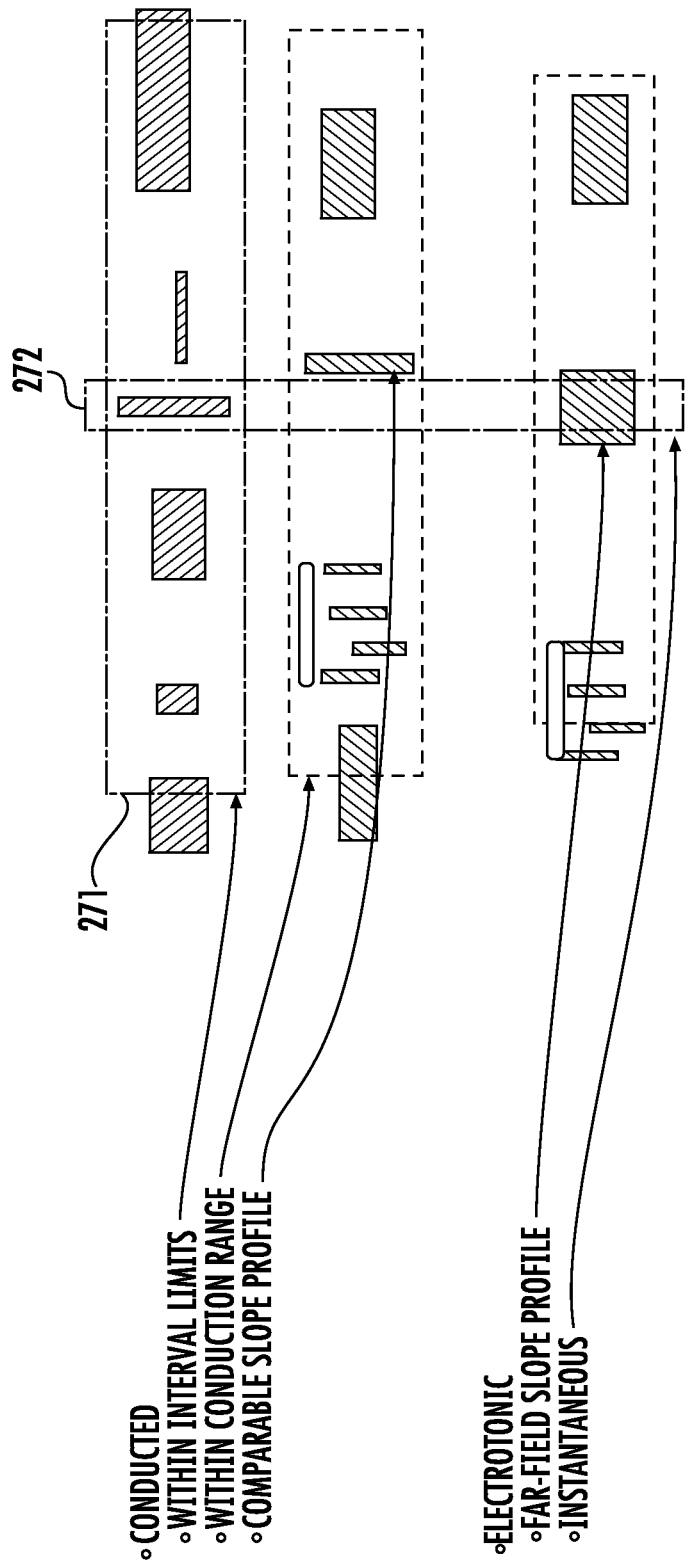
FIGS. 27-29 show example AF mapping spatio-temporal slope analysis.
Figure 28:
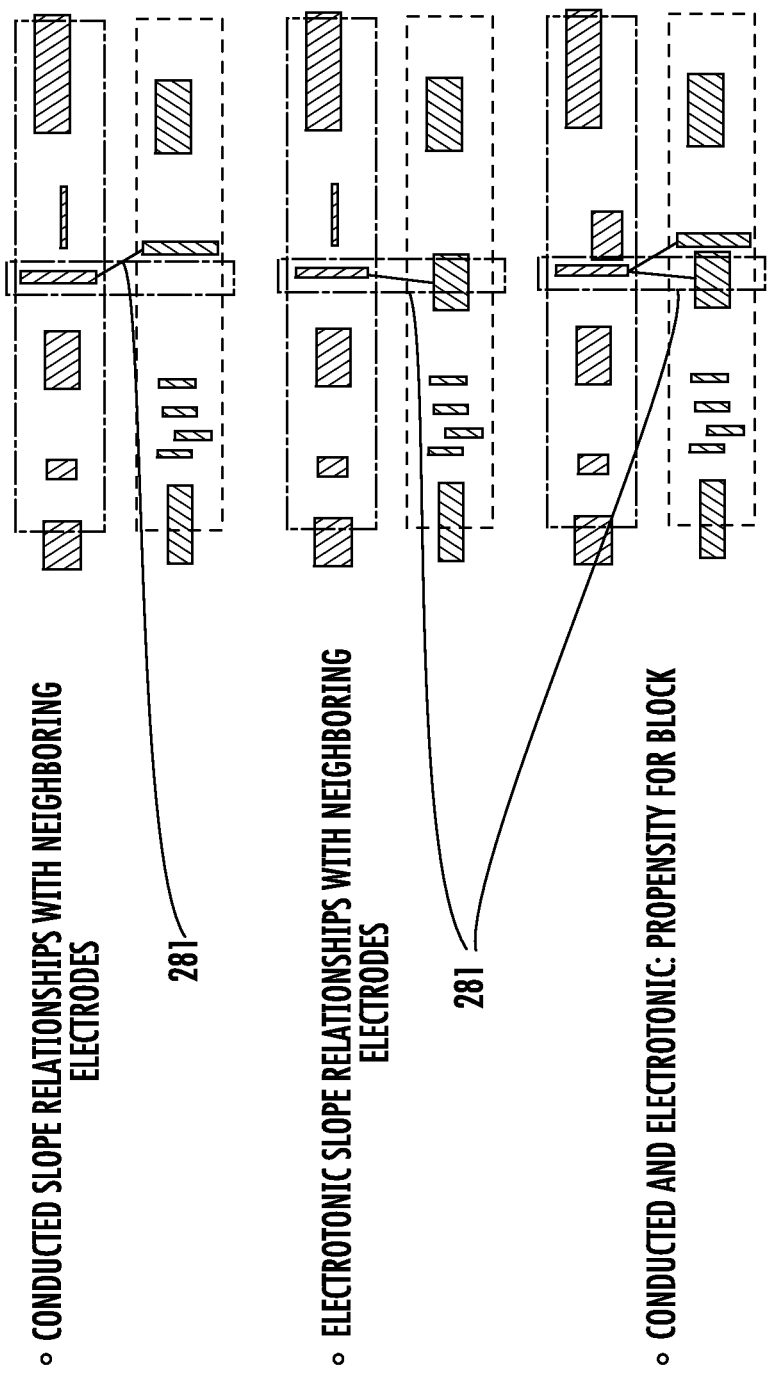
Figure 29:
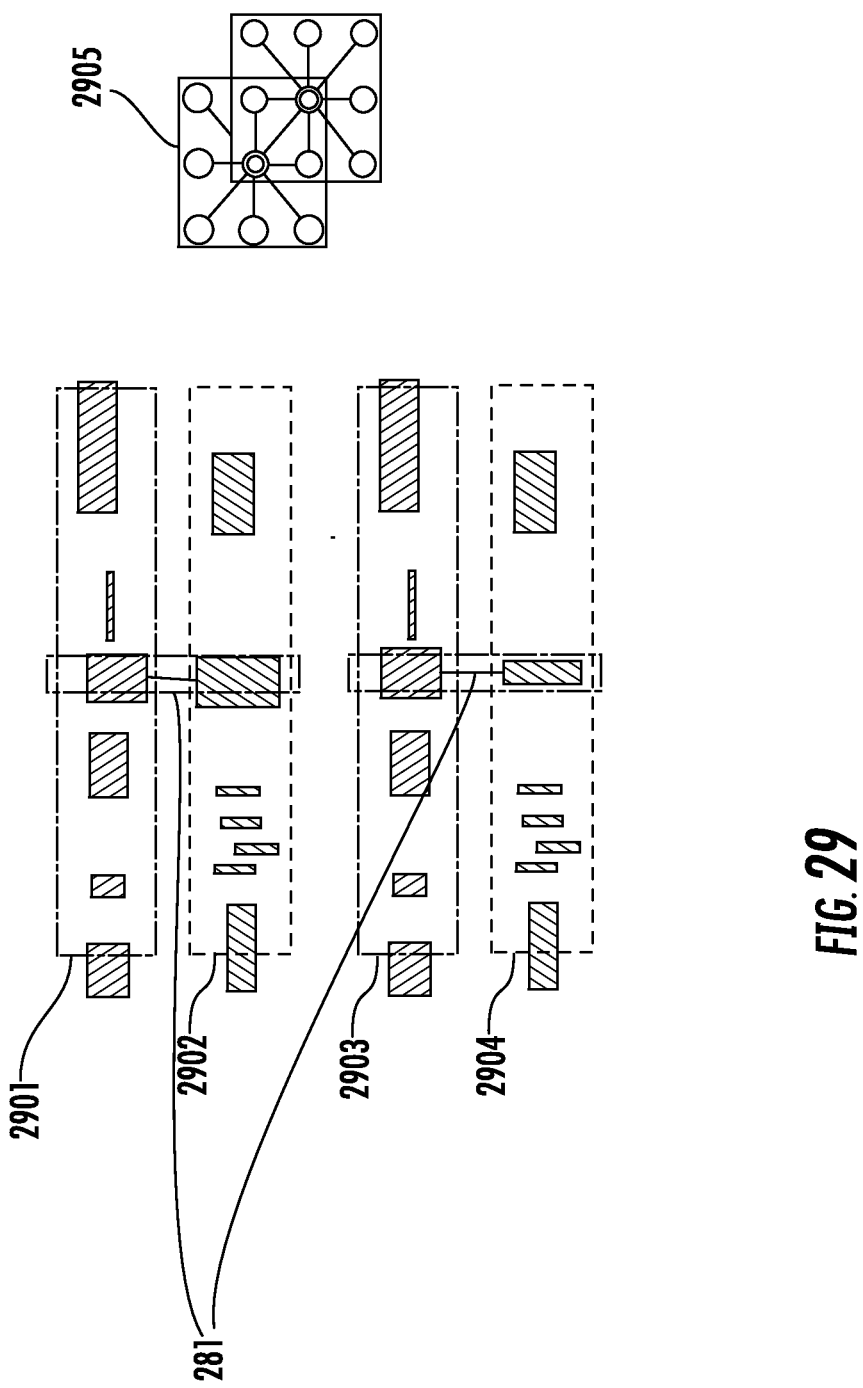

FIGS. 27-29 show AF mapping spatio-temporal slope analysis which can be used to provide additional evidence regarding an acquired ECG 302 and whether or not portions of it are fractionated. Spatio-temporal relations are assessed between the slopes of center electrodes C and the slopes of neighboring electrodes 1-8. Spatio-temporal relations are identified between the center electrode slope 261 and the slopes in each of the neighboring electrode IC ECGs 264.

FIG. 27 shows the center electrode slopes 261 as graphs of conducted and electrotonic acquired ECG signals 302. The dashed boxes represent the search windows for either conducted 271 (wide window) or electrotonic 272 (narrow window) relationships. Conducted relationships 271 comprise elements within interval limits, within conduction range and comparable slope profile. Electrotonic relationships 272 comprise far field slope profile and are instantaneous. Conducted window width 263 typically depends on conduction velocity and center-to-neighboring electrode distance. The more relations that can be made between the center electrode C and the eight neighboring electrodes 1-8, the higher the evidence of correct annotation of the slope of the center electrode C will be.

FIGS. 28 and 29 show specific examples of conducted, electrotonic and combined electrotonic and conducted relationships between the center electrode slope profile 261 and one of the neighbors.

FIG. 28 shows graphs for determining the slope relationships of center electrode C versus neighbor electrodes 1-8. Both conducted or electrotonic relationships found increased evidence that the primary slope being tested is related to a single potential. As shown in the graphs, single potential evidence increases in the case of: 1) conducted slope relationships with neighboring electrodes (top two graphs); 2) electronic slope relationships with neighboring electrodes (middle two graphs); and 3) the combination of conducted and electronic propensity for block (bottom two graphs). The line 281 indicates a time shift of the center neighboring slope within the window, indicating their conducted relationship.

FIG. 29, shows a far field slope related to an electrotonic (top) or primary slope (bottom). Far field potential evidence can increase in the case of three factors as shown. A first factor can be electrotonic slope relationships with neighboring electrodes and maximum one single potential indicated slope. Note that this factor can either be based on slope initial characteristic (T*, E*) or as a result from slope type earlier assignment (T,E). A second factor can be either FF indicated, as shown in the top two graphs 2901, 2902, or only single potentials, as shown in the bottom two graphs 2903, 2904. Finally, if only electronic slope relationships are found, the propensity is for (temporary) non-contact electrode or far field (e.g. ventricular). The right side of FIG. 29 graphically illustrates a spatial difference between the measurements of 2 different electrode groups 2905.

It should be understood that many variations are possible based on the disclosure herein. Although features and elements are described above in particular combinations, each feature or element can be used alone without the other features and elements or in various combinations with or without other features and elements.

The methods provided include implementation in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements methods described herein.

The methods or flow charts provided herein can be implemented in a computer program, software, or firmware incorporated in a non-transitory computer-readable storage medium for execution by a general purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A computer implemented method of determining regions of interest for cardiac ablation using fractionation which improves performance of a processing system, the method comprising:
   detecting, via a plurality of sensors, electro-cardiogram (ECG) signals, each ECG signal detected via one of the plurality of sensors and indicating electrical activity of a heart;
   determining, for each of the plurality of ECG signals, one or more local activation times (LATs) each indicating a time of activation of a corresponding ECG signal;
   generating, based on the determined one or more LATs of each of the plurality of ECG signals, one or more driver maps and one or more perpetuator maps, each representing the electrical activity of the heart;
   deriving parameters, comprising fractionated ECG signal potentials, from the perpetuator maps by:
      comparing an ECG signal potential within a fractionation window to a plurality of stored signal potential templates;
      selecting one of the stored signal potential templates according to a level of resemblance to the ECG signal within the fractionation window; and
      displaying a mapping, using the derived parameters, which indicates driver evidence and perpetuator evidence of areas of fractionation,
   wherein the regions of interest for cardiac ablation are determined in accordance with the areas of fractionation.

2. The method of claim 1, further comprising:
   deriving the parameters by:
      filtering the LATs and removing non-fractionated LATs comprising non-fractionated single potentials, short double potentials and long double potentials.

3. The method of claim 1, further comprising displaying, on a display device, the regions of interest.

4. A computer implemented method of determining regions of interest for cardiac ablation using fractionation which improves performance of a processing system, the method comprising:
  detecting, via a plurality of sensors, electro-cardiogram (ECG) signals, each ECG signal detected via one of the plurality of sensors and indicating electrical activity of a heart;
  determining, for each of the plurality of ECG signals, one or more local activation times (LATs) each indicating a time of activation of a corresponding ECG signal;
  generating, based on the determined one or more LATs of each of the plurality of ECG signals, one or more driver maps and one or more perpetuator maps, each representing the electrical activity of the heart;
  deriving parameters, comprising fractionated ECG signal potentials, from the perpetuator maps by:
    determining peaks and valleys of an ECG signal within windows of fractionation;
    calculating a number of fractionation slopes of the ECG signal between the peaks and valleys of the ECG ECG signal;
    comparing the number of fractionation slopes to a predetermined threshold;
    determining an ECG signal to be a fractionated signal if the number of fractionation slopes is greater than a predetermined threshold; and
    displaying a fractionation map of the ECG signal, wherein the regions of interest for cardiac ablation are determined from the fractionation map.

5. The method of claim 4, further comprising:
  calculating incidence using the detected peak valleys;
  calculating incidence fractionation far field for single potential slopes using the incidence.

6. The method of claim 4, further comprising:
  converting slopes between the peaks and valleys into potentials using a time gate comprising temporal grouping of primary and secondary slopes;
  grouping the potentials into groups of consecutive slopes within a predetermined interval; and
  analyzing the potentials as slope types in accordance with the groupings.

7. The method of claim 6, wherein each group comprises one of a single slope group, a short double slope group, a long double slope group and a two slope group.

8. A system of determining regions of interest for cardiac ablation using fractionation which improves processing performance, the system comprising:
  a plurality of sensors, each configured to detect one of a plurality of electro-cardiogram (ECG) signals over time, each ECG signal indicating electrical activity of a heart;
  a processing device comprising one or more processor configured to:
    determine, for each of the plurality of ECG signals, one or more local activation times (LATs) each indicating a time of activation of a corresponding ECG signal;
    generate, based on the determined one or more LATs of each of the plurality of ECG signals, one or more driver maps and one or more perpetuator maps, each representing the electrical activity of the heart;
    derive parameters, comprising fractionated ECG signal potentials, from the perpetuator maps by;
      comparing an ECG signal potential within a fractionation window to a plurality of stored signal potential templates; and
      selecting one of the stored signal potential templates according to a level of resemblance to the ECG signal within the fractionation window; and
  a display device configured to display a mapping, using the derived parameters, which indicates driver evidence and perpetuator evidence of areas of fractionation, wherein the regions of interest for cardiac ablation are determined in accordance with the areas of fractionation.

9. The system of claim 8, wherein the processing device is further configured to:
  deriving the parameters by:
    filtering the LATs and removing non-fractionated LATs comprising non-fractionated single potentials, short double potentials and long double potentials.

10. The system of claim 8, wherein the display device is configured to display the regions of interest.

11. A system of determining regions of interest for cardiac ablation using fractionation which improves processing performance, the system comprising:
  a plurality of sensors, each configured to detect one of a plurality of electro-cardiogram (ECG) signals over time, each ECG signal indicating electrical activity of a heart;
  a processing device configured to:
    detect, via a plurality of sensors, electro-cardiogram (ECG) signals, each ECG signal detected via one of the plurality of sensors and indicating electrical activity of a heart;
    determine, for each of the plurality of ECG signals, one or more local activation times (LATs) each indicating a time of activation of a corresponding ECG signal;
    generate, based on the determined one or more LATs of each of the plurality of ECG signals, one or more driver maps and one or more perpetuator maps, each representing the electrical activity of the heart;
    derive parameters, comprising fractionated ECG signal potentials, from the perpetuator maps by:
      determining peaks and valleys of an ECG signal within windows of fractionation;
      calculating a number of fractionation slopes of the ECG signal between the peaks and valleys of the ECG ECG signal;
      comparing the number of fractionation slopes to a predetermined threshold;
      determining an ECG signal to be a fractionated signal if the number of fractionation slopes is greater than a predetermined threshold; and
      displaying a fractionation map of the ECG signal, wherein the regions of interest for cardiac ablation are determined from the fractionation map.

12. The system of claim 11, wherein the processing device is further configured to:
  calculate incidence using the detected peak valleys;
  calculate incidence fractionation far field for single potential slopes using the incidence.

13. The system of claim 11, wherein the processing device is further configured to:
  convert slopes between the peaks and valleys into potentials using a time gate comprising temporal grouping of primary and secondary slopes;
  group the potentials into groups of consecutive slopes within a predetermined interval; and
  analyze the potentials as slope types in accordance with the groupings.

14. The system of claim 13, wherein each group comprises one of a single slope group, a short double slope group, a long double slope group and a two slope group.

* * * * *

UNITED STATES PATENT AND TRADEMARK OFFICE
CERTIFICATE OF CORRECTION

| | | |
|---|---|---|
| PATENT NO. | : 10,314,542 B2 | |
| APPLICATION NO. | : 15/404244 | |
| DATED | : June 11, 2019 | |
| INVENTOR(S) | : Meir Bar-Tal et al. | |

It is certified that error appears in the above-identified patent and that said Letters Patent is hereby corrected as shown below:

On the Title Page
Item (57), under "ABSTRACT", in Column 2, Line 6, delete "activation" and insert -- local activation --, therefor.

In the Drawings
In Fig. 17, Sheet 18 of 30, delete "ICECGs" and insert -- IC ECGs --, therefor.
In Fig. 22, Sheet 23 of 30, for Tag "2224", in Line 1, delete "FAR FAR FIELD" and insert -- FAR FIELD --, therefor.

In the Specification
In Column 2, Line 16, delete "The the" and insert -- The --, therefor.
In Column 5, Line 39, delete "focal sources 108" and insert -- focal sources 112 --, therefor.
In Column 6, Line 54, delete "FIG. 3A, The" and insert -- FIG. 3A. The --, therefor.
In Column 7, Line 62, delete "shown" and insert -- shown in --, therefor.
In Column 10, Line 45, delete "shown in" and insert -- shown on --, therefor.
In Column 11, Line 18, delete "8, 12 16" and insert -- 8, 12, 16 --, therefor.
In Column 11, Line 47, delete "second template 112b" and insert -- second template 1112b --, therefor.
In Column 12, Line 35, delete "signal" and insert -- signal. --, therefor.
In Column 13, Line 2, delete "paramenters" and insert -- parameters --, therefor.
In Column 13, Line 4, delete "paramenters" and insert -- parameters --, therefor.
In Column 14, Line 15, delete "2207." and insert -- 2207). --, therefor.
In Column 14, Line 33, delete "time gate 2209" and insert -- time gate 2204 --, therefor.
In Column 15, Line 47, delete "FIG. 29," and insert -- FIG. 29 --, therefor.

In the Claims
In Column 17, Lines 22-23, in Claim 4, delete "ECG ECG signal;" and insert -- ECG signal; --, therefor.
In Column 18, Lines 44-45, in Claim 11, delete "ECG ECG signal;" and insert -- ECG signal; --, therefor.

Signed and Sealed this
Twenty-first Day of February, 2023

*Katherine Kelly Vidal*

Katherine Kelly Vidal
*Director of the United States Patent and Trademark Office*